United States Patent
Hughes

(10) Patent No.: US 12,145,965 B2
(45) Date of Patent: Nov. 19, 2024

(54) USE OF VITELLOGENIN FOR DEFINING AND TESTING NOVEL IMMUNOGENS IN INSECTS

(71) Applicant: Dalan Animal Health, Inc., Athens, GA (US)

(72) Inventor: Huw Hughes, Los Angeles, CA (US)

(73) Assignee: Dalan Animal Health, Inc., Athens, GA (US)

( * ) Notice: Subject to any disclaimer, the term of this patent is extended or adjusted under 35 U.S.C. 154(b) by 0 days.

(21) Appl. No.: 18/043,723

(22) PCT Filed: Sep. 1, 2021

(86) PCT No.: PCT/US2021/048727
§ 371 (c)(1),
(2) Date: Mar. 1, 2023

(87) PCT Pub. No.: WO2022/051406
PCT Pub. Date: Mar. 10, 2022

(65) Prior Publication Data
US 2024/0018183 A1 Jan. 18, 2024

Related U.S. Application Data

(60) Provisional application No. 63/074,365, filed on Sep. 3, 2020.

(51) Int. Cl.
*C07K 1/16* (2006.01)
*C07K 14/435* (2006.01)

(52) U.S. Cl.
CPC .......... *C07K 1/16* (2013.01); *C07K 14/43572* (2013.01)

(58) Field of Classification Search
CPC ...... C07K 1/16; C07K 14/43572; A61P 31/00
See application file for complete search history.

(56) References Cited

U.S. PATENT DOCUMENTS

| 10,994,001 B2 | 5/2021 | Salmela et al. |
| 2016/0032252 A1 | 2/2016 | Evans et al. |
| 2021/0275658 A1 | 9/2021 | Salmela et al. |
| 2022/0354940 A1 | 11/2022 | Freitak et al. |

FOREIGN PATENT DOCUMENTS

| WO | WO-2017/017313 | 2/2017 |
| WO | WO-2017/017313 A1 | 2/2017 |
| WO | WO-2021/055625 | 3/2021 |
| WO | WO-2022/192752 | 9/2022 |

OTHER PUBLICATIONS

Salmela et al. "Transfer of immunity from mother to offspring is mediated via egg-yolk protein vitellogenin" PLOS Pathogens: pp. 1-12, Jul. 31, 2015 (Year: 2015).*
International Search Report and Written Opinion for PCT/US2021/048727, dated Jan. 18, 2022, 11 pages.
Marheineke et al., "Lipid Composition of Spodoptera Frugiperda (sf9) and Trichoplusia Ni (tn) Insect Cells Used for Baculovirus Infection", FEBS Letters, Dec. 11, 1998, vol. 441, No. 1, pp. 49-52, DOI: 10.1016/s0014-5793(98)01523-3.
Nose et al., "Cloning of cDNA for vitellogenin of the Parasitoid Wasp, *Pimpla nipponica* (Hymenoptera: Apocrita: Ichneumonidae): Vitellogenin Primary Structure and Evolutionary Considerations", Insect Biochemistry and Molecular Biology, Dec. 1987, vol. 27, No. 12, pp. 1047-1056, DOI: 10.1016/s0965-1748(97)00091-x.
Byhro et al., "Different activation of immune-related genes in honey bee nurses and foragers (*Apis mellifera*)", Apidologie, 50(4):463-471 (Jun. 20, 2019).
Extended European Search Report on EP 21865059.6 DTD Mar. 21, 2024, 11 pages.

* cited by examiner

*Primary Examiner* — Nelson B Moseley, II
*Assistant Examiner* — Alyssa Rae Stonebraker
(74) *Attorney, Agent, or Firm* — Foley & Lardner LLP

(57) ABSTRACT

The present invention relates to methods of isolating a honey bee antigen that could be useful as a vaccine. The present invention further relates to proteomic methods of identifying antigenic proteins.

11 Claims, 4 Drawing Sheets

Specification includes a Sequence Listing.

| Signal Peptide | Vitellogenin | His |

SEQUENCE LISTING

<160> NUMBER OF SEQ ID NOS: 2

<210> SEQ ID NO 1
<211> LENGTH: 1778
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Leu Leu Leu Leu Thr Leu Leu Leu Phe Ala Gly Thr Val Ala Ala
1               5                   10                  15

Asp Phe Gln His Asn Trp Gln Val Gly Asn Glu Tyr Thr Tyr Leu Val
                20                  25                  30

Arg Ser Arg Thr Leu Thr Ser Leu Gly Asp Leu Ser Asp Val His Thr
            35                  40                  45

Gly Ile Leu Ile Lys Ala Leu Leu Thr Val Gln Ala Lys Asp Ser Asn
        50                  55                  60

Val Leu Ala Ala Lys Val Trp Asn Gly Gln Tyr Ala Arg Val Gln Gln
65                  70                  75                  80

Ser Met Pro Asp Gly Trp Glu Thr Glu Ile Ser Asp Gln Met Leu Glu
                85                  90                  95

Leu Arg Asp Leu Pro Ile Ser Gly Lys Pro Phe Gln Ile Arg Met Lys
                100                 105                 110

His Gly Leu Ile Arg Asp Leu Ile Val Asp Arg Asp Val Pro Thr Trp
            115                 120                 125

```
Glu Val Asn Ile Leu Lys Ser Ile Val Gly Gln Leu Gln Val Asp Thr
    130                 135                 140
Gln Gly Glu Asn Ala Val Lys Val Asn Ser Val Gln Val Pro Thr Asp
145                 150                 155                 160
Asp Glu Pro Tyr Ala Ser Phe Lys Ala Met Glu Asp Ser Val Gly Gly
                165                 170                 175
Lys Cys Glu Val Leu Tyr Asp Ile Ala Pro Leu Ser Asp Phe Val Ile
                180                 185                 190
His Arg Ser Pro Glu Leu Val Pro Met Pro Thr Leu Lys Gly Asp Gly
            195                 200                 205
Arg His Met Glu Val Ile Lys Ile Lys Asn Phe Asp Asn Cys Asp Gln
    210                 215                 220
Arg Ile Asn Tyr His Phe Gly Met Thr Asp Asn Ser Arg Leu Glu Pro
225                 230                 235                 240
Gly Thr Asn Lys Asn Gly Lys Phe Phe Ser Arg Ser Thr Ser Ser Arg
                245                 250                 255
Ile Val Ile Ser Glu Ser Leu Lys His Phe Thr Ile Gln Ser Ser Val
                260                 265                 270
Thr Thr Ser Lys Met Met Val Ser Pro Arg Leu Tyr Asp Arg Gln Asn
            275                 280                 285
Gly Leu Val Leu Ser Arg Met Asn Leu Thr Leu Ala Lys Met Glu Lys
    290                 295                 300
Thr Ser Lys Pro Leu Pro Met Val Asp Asn Pro Glu Ser Thr Gly Asn
305                 310                 315                 320
Leu Val Tyr Ile Tyr Asn Asn Pro Phe Ser Asp Val Glu Glu Arg Arg
                325                 330                 335
Val Ser Lys Thr Ala Met Asn Ser Asn Gln Ile Val Ser Asp Asn Ser
                340                 345                 350
Leu Ser Ser Ser Glu Glu Lys Leu Lys Gln Asp Ile Leu Asn Leu Arg
            355                 360                 365
Thr Asp Ile Ser Ser Ser Ser Ser Ile Ser Ser Ser Glu Glu Asn
    370                 375                 380
Asp Phe Trp Gln Pro Lys Pro Thr Leu Glu Asp Ala Pro Gln Asn Ser
385                 390                 395                 400
Leu Leu Pro Asn Phe Val Gly Tyr Lys Gly Lys His Ile Gly Lys Ser
                405                 410                 415
Gly Lys Val Asp Val Ile Asn Ala Ala Lys Glu Leu Ile Phe Gln Ile
                420                 425                 430
Ala Asn Glu Leu Glu Asp Ala Ser Asn Ile Pro Val His Ala Thr Leu
            435                 440                 445
Glu Lys Phe Met Ile Leu Cys Asn Leu Met Arg Thr Met Asn Arg Lys
    450                 455                 460
Gln Ile Ser Glu Leu Glu Ser Asn Met Gln Ile Ser Pro Asn Glu Leu
465                 470                 475                 480
Lys Pro Asn Asp Lys Ser Gln Val Ile Lys Gln Asn Thr Trp Thr Val
                485                 490                 495
Phe Arg Asp Ala Ile Thr Gln Thr Gly Thr Gly Pro Ala Phe Leu Thr
                500                 505                 510
Ile Lys Glu Trp Ile Glu Arg Gly Thr Thr Lys Ser Met Glu Ala Ala
            515                 520                 525
Asn Ile Met Ser Lys Leu Pro Lys Thr Val Arg Thr Pro Thr Asp Ser
    530                 535                 540
```

```
Tyr Ile Arg Ser Phe Phe Glu Leu Leu Gln Asn Pro Lys Val Ser Asn
545                 550                 555                 560

Glu Gln Phe Leu Asn Thr Ala Ala Thr Leu Ser Phe Cys Glu Met Ile
                565                 570                 575

His Asn Ala Gln Val Asn Lys Arg Ser Ile His Asn Asn Tyr Pro Val
            580                 585                 590

His Thr Phe Gly Arg Leu Thr Ser Lys His Asp Asn Ser Leu Tyr Asp
        595                 600                 605

Glu Tyr Ile Pro Phe Leu Arg Glu Leu Arg Lys Ala His Gln Glu
    610                 615                 620

Lys Asp Ser Pro Arg Ile Gln Thr Tyr Ile Met Ala Leu Gly Met Ile
625                 630                 635                 640

Gly Glu Pro Lys Ile Leu Ser Val Phe Glu Pro Tyr Leu Glu Gly Lys
                645                 650                 655

Gln Gln Met Thr Val Phe Gln Arg Thr Leu Met Val Gly Ser Leu Gly
            660                 665                 670

Lys Leu Thr Glu Thr Asn Pro Lys Leu Ala Arg Ser Val Leu Tyr Lys
        675                 680                 685

Ile Tyr Leu Asn Thr Met Glu Ser His Glu Val Arg Cys Thr Ala Val
690                 695                 700

Phe Leu Leu Met Lys Thr Asn Pro Pro Leu Ser Met Leu Gln Arg Met
705                 710                 715                 720

Ala Glu Phe Thr Lys Leu Asp Thr Asn Arg Gln Val Asn Ser Ala Val
                725                 730                 735

Lys Ser Thr Ile Gln Ser Leu Met Lys Leu Lys Ser Pro Glu Trp Lys
            740                 745                 750

Asp Leu Ala Lys Lys Ala Arg Ser Val Asn His Leu Leu Thr His His
        755                 760                 765

Glu Tyr Asp Tyr Glu Leu Ser Arg Gly Tyr Ile Asp Glu Lys Ile Leu
    770                 775                 780

Glu Asn Gln Asn Ile Ile Thr His Met Ile Leu Asn Tyr Val Gly Ser
785                 790                 795                 800

Glu Asp Ser Val Ile Pro Arg Ile Leu Tyr Leu Thr Trp Tyr Ser Ser
                805                 810                 815

Asn Gly Asp Ile Lys Val Pro Ser Thr Lys Val Leu Ala Met Ile Ser
            820                 825                 830

Ser Val Lys Ser Phe Met Glu Leu Ser Leu Arg Ser Val Lys Asp Arg
        835                 840                 845

Glu Thr Ile Ile Ser Ala Ala Glu Lys Ile Ala Glu Glu Leu Lys Ile
    850                 855                 860

Val Pro Glu Glu Leu Val Pro Leu Glu Gly Asn Leu Met Ile Asn Asn
865                 870                 875                 880

Lys Tyr Ala Leu Lys Phe Phe Pro Phe Asp Lys His Ile Leu Asp Lys
                885                 890                 895

Leu Pro Thr Leu Ile Ser Asn Tyr Ile Glu Ala Val Lys Glu Gly Lys
            900                 905                 910

Phe Met Asn Val Asn Met Leu Asp Thr Tyr Glu Ser Val His Ser Phe
        915                 920                 925

Pro Thr Glu Thr Gly Leu Pro Phe Val Tyr Thr Phe Asn Val Ile Lys
    930                 935                 940

Leu Thr Lys Thr Ser Gly Thr Val Gln Ala Gln Ile Asn Pro Asp Phe
945                 950                 955                 960

Ala Phe Ile Val Asn Ser Asn Leu Arg Leu Thr Phe Ser Lys Asn Val
```

-continued

```
            965                 970                 975
Gln Gly Arg Val Gly Phe Val Thr Pro Phe Glu His Arg His Phe Ile
                980                 985                 990
Ser Gly Ile Asp Ser Asn Leu His  Val Tyr Ala Pro Leu  Lys Ile Ser
            995                1000                1005
Leu Asp Val Asn Thr Pro Lys  Gly Asn Met Gln Trp  Lys Ile Trp
     1010                1015                1020
Pro Met Lys Gly Glu Glu Lys  Ser Arg Leu Phe His  Tyr Ser Val
     1025                1030                1035
Val Pro Phe Val Ser Asn His  Asp Ile Leu Asn Leu  Arg Pro Leu
     1040                1045                1050
Ser Met Glu Lys Gly Thr Arg  Pro Met Ile Pro Asp  Asp Asn Thr
     1055                1060                1065
Ser Leu Ala Leu Pro Lys Asn  Glu Gly Pro Phe Arg  Leu Asn Val
     1070                1075                1080
Glu Thr Ala Lys Thr Asn Glu  Glu Met Trp Glu Leu  Ile Asp Thr
     1085                1090                1095
Glu Lys Leu Thr Asp Arg Leu  Pro Tyr Pro Trp Thr  Met Asp Asn
     1100                1105                1110
Glu Arg Tyr Val Lys Val Asp  Met Tyr Met Asn Leu  Glu Gly Glu
     1115                1120                1125
Gln Lys Asp Pro Val Ile Phe  Ser Thr Ser Phe Asp  Ser Lys Val
     1130                1135                1140
Met Thr Arg Pro Asp Thr Asp  Ser Glu Asn Trp Thr  Pro Lys Met
     1145                1150                1155
Met Ala Val Glu Pro Thr Asp  Lys Gln Ala Asn Ser  Lys Thr Arg
     1160                1165                1170
Arg Gln Glu Met Met Arg Glu  Ala Gly Arg Gly Ile  Glu Ser Ala
     1175                1180                1185
Lys Ser Tyr Val Val Asp Val  Arg Val His Val Pro  Gly Glu Ser
     1190                1195                1200
Glu Ser Glu Thr Val Leu Thr  Leu Ala Trp Ser Glu  Ser Asn Val
     1205                1210                1215
Glu Ser Lys Gly Arg Leu Leu  Gly Phe Trp Arg Val  Glu Met Pro
     1220                1225                1230
Arg Ser Asn Ala Asp Tyr Glu  Val Cys Ile Gly Ser  Gln Ile Met
     1235                1240                1245
Val Ser Pro Glu Thr Leu Leu  Ser Tyr Asp Glu Lys  Met Asp Gln
     1250                1255                1260
Lys Pro Lys Met Asp Phe Asn  Val Asp Ile Arg Tyr  Gly Lys Asn
     1265                1270                1275
Cys Gly Lys Gly Glu Arg Ile  Asp Met Asn Gly Lys  Leu Arg Gln
     1280                1285                1290
Ser Pro Arg Leu Lys Glu Leu  Val Gly Ala Thr Ser  Ile Ile Lys
     1295                1300                1305
Asp Cys Val Glu Asp Met Lys  Arg Gly Asn Lys Ile  Leu Arg Thr
     1310                1315                1320
Cys Gln Lys Ala Val Val Leu  Ser Met Leu Leu Asp  Glu Val Asp
     1325                1330                1335
Ile Ser Met Glu Val Pro Asp  Ala Leu Ile Ala Leu  Tyr Ser
     1340                1345                1350
Gln Gly Leu Phe Ser Leu Ser  Glu Ile Asp Asn Leu  Asp Val Ser
     1355                1360                1365
```

```
Leu Asp Val Ser Asn Pro Lys Asn Ala Gly Lys Lys Ile Asp
1370             1375             1380

Val Arg Ala Lys Leu Asn Glu Tyr Leu Asp Lys Ala Asp Val Ile
1385             1390             1395

Val Asn Thr Pro Ile Met Asp Ala His Phe Lys Asp Val Lys Leu
1400             1405             1410

Ser Asp Phe Gly Phe Ser Thr Glu Asp Ile Leu Asp Thr Ala Asp
1415             1420             1425

Glu Asp Leu Leu Ile Asn Asn Val Phe Tyr Glu Asp Glu Thr Ser
1430             1435             1440

Cys Met Leu Asp Lys Thr Arg Ala Gln Thr Phe Asp Gly Lys Asp
1445             1450             1455

Tyr Pro Leu Arg Leu Gly Pro Cys Trp His Ala Val Met Thr Thr
1460             1465             1470

Tyr Pro Arg Ile Asn Pro Asp Asn His Asn Glu Lys Leu His Ile
1475             1480             1485

Pro Lys Asp Lys Ser Val Ser Val Leu Ser Arg Glu Asn Glu Ala
1490             1495             1500

Gly Gln Lys Glu Val Lys Val Leu Leu Gly Ser Asp Lys Ile Lys
1505             1510             1515

Phe Val Pro Gly Thr Thr Ser Gln Pro Glu Val Phe Val Asn Gly
1520             1525             1530

Glu Lys Ile Val Val Ser Arg Asn Lys Ala Tyr Gln Lys Val Glu
1535             1540             1545

Glu Asn Glu Ile Ile Phe Glu Ile Tyr Lys Met Gly Asp Arg Phe
1550             1555             1560

Ile Gly Leu Thr Ser Asp Lys Phe Asp Val Ser Leu Ala Leu Asp
1565             1570             1575

Gly Glu Arg Val Met Leu Lys Ala Ser Glu Asp Tyr Arg Tyr Ser
1580             1585             1590

Val Arg Gly Leu Cys Gly Asn Phe Asp His Asp Ser Thr Asn Asp
1595             1600             1605

Phe Val Gly Pro Lys Asn Cys Leu Phe Arg Lys Pro Glu His Phe
1610             1615             1620

Val Ala Ser Tyr Ala Leu Ile Ser Asn Gln Cys Glu Gly Asp Ser
1625             1630             1635

Leu Asn Val Ala Lys Ser Leu Gln Asp His Asp Cys Ile Arg Gln
1640             1645             1650

Glu Arg Thr Gln Gln Arg Asn Val Ile Ser Asp Ser Glu Ser Gly
1655             1660             1665

Arg Leu Asp Thr Glu Met Ser Thr Trp Gly Tyr His His Asn Val
1670             1675             1680

Asn Lys His Cys Thr Ile His Arg Thr Gln Val Lys Glu Thr Asp
1685             1690             1695

Asp Lys Ile Cys Phe Thr Met Arg Pro Val Val Ser Cys Ala Ser
1700             1705             1710

Gly Cys Thr Ala Val Glu Thr Lys Ser Lys Pro Tyr Lys Phe His
1715             1720             1725

Cys Met Glu Lys Asn Glu Ala Ala Met Lys Leu Lys Lys Arg Ile
1730             1735             1740

Glu Lys Gly Ala Asn Pro Asp Leu Ser Gln Lys Pro Val Ser Thr
1745             1750             1755
```

| Thr | Glu | Glu | Leu | Thr | Val | Pro | Phe | Val | Cys | Lys | Ala | His | His | His |
|---|---|---|---|---|---|---|---|---|---|---|---|---|---|---|
| 1760 | | | | | 1765 | | | | | 1770 | | | | |

| His | His | His | His | His |
|---|---|---|---|---|
| 1775 | | | | |

<210> SEQ ID NO 2
<211> LENGTH: 5361
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
gaattcgccg ccaccatgct gctgctgctg actctgctgc tgttcgctgg taccgtggct      60
gccgacttcc agcacaactg gcaggtcggc aacgagtaca cctacctggt gcgctctcgt     120
accctgactt cactgggcga cctgtccgac gtccacactg gaatcctgat caaggctctg     180
ctgaccgtgc aggccaagga ctctaacgtc tggctgccaa agtgtggaa cggccagtac      240
gctcgtgtgc agcagtccat gcccgacgga tgggagactg aaatcagcga ccagatgctg     300
gaactgcgtg acctgccaat ctcaggcaag cctttccaga tcaggatgaa gcacggactg     360
atcagggacc tgatcgtcga cagagacgtg ccaacctggg aggtgaacat cctgaagtct     420
atcgtcggtc agctgcaggt ggacactcag ggcgaaaacg ctgtgaaggt caactcagtc     480
caggtcccca ccgacgacga gccatacgct tccttcaagg ccatggaaga cagcgtcggt     540
ggcaagtgcg aggtgctgta cgacatcgcc cctctgtctg acttcgtcat ccaccgttca     600
cccgaactgg tgccaatgcc taccctgaag ggagacggta ggcacatgga ggtcatcaag     660
atcaagaact cgacaactg cgaccagaga tcaactacc acttcggtat gactgacaac      720
agccgcctgg aaccaggtac caacaagaac ggcaagttct tcagccgctc cagcacttct     780
cgtatcgtga ctccgagag cctgaagcac ttcaccatcc aatcttcagt caccacttca     840
aagatgatgg tgtcccctag gctgtacgac agacagaacg gtctggtcct gtcccgtatg     900
aacctgactc tggctaagat ggaaaagacc tctaagcccc tgccaatggt cgacaaccct     960
gagtcaactg gcaacctggt gtacatctac aacaacccct tcagcgacgt cgaggaacgc    1020
cgtgtgagca agaccgccat gaactctaac cagatcgtgt cagacaactc cctgtccagc    1080
tctgaggaaa agctgaaaca ggacatcctg aacctgagga ctgacatctc atccagctct    1140
tcatccatca gctcttcaga ggaaaacgac ttctggcagc ctaagcccac cctggaggac    1200
gctccacaga actccctgct gcctaacttc gtgggctaca agggaaagca catcggcaag    1260
agcggcaagg tggacgtcat caacgctgcc aaggaactga tcttccagat cgctaacgaa    1320
ctggaagacg cctccaacat cccagtccac gccactctgg agaagttcat gatcctgtgc    1380
aacctgatgc gcaccatgaa ccgtaagcag atctcagagc tggaatccaa catgcagatc    1440
tctcctaacg aactgaagcc caacgacaag tcacaggtca tcaagcagaa cacctggact    1500
gtgttcagag acgctatcac ccagactggc accggacctg ccttcctgac tatcaaggaa    1560
tggatcgagc gcggtaccac taagtctatg gagctgcca acatcatgtc aaagctgccc    1620
aagaccgtga ggactccaac cgacagctac atcgatctt tcttcgaact gctgcagaac    1680
cctaaggtgt ccaacgagca gttcctgaac actgctgcca ccctgagctt ctgcgagatg    1740
atccacaacg ctcaggtcaa caagagaagc atccacaaca ctaccccgt gcacactttc    1800
ggccgcctga ccagcaagca cgacaactct ctgtacgacg aatacatccc tttcctggag    1860
```

```
agggaactga gaaaggccca ccaggagaag gactccccccc gtatccagac ctacatcatg    1920
gctctgggaa tgatcggtga accaaagatc ctgagcgtgt tcgaaccta cctggaggga     1980 aagcagcaga tgactgtctt ccagaggacc ctgatggtgg gctctctggg aaagctgact    2040
gaaaccaacc ccaagctggc ccgttctgtc ctgtacaaga tctacctgaa cactatggaa    2100
tcacacgagg tcaggtgcac tgctgtgttc ctgctgatga agaccaaccc tcccctgtca    2160
atgctgcagc gtatggccga gttcactaag ctggacacca acaggcaggt caactcagct    2220
gtgaagtcca ccatccagag cctgatgaag ctgaagtccc cagagtggaa ggacctggct    2280
aagaaggcca aagcgtgaa ccacctgctg actcaccacg aatacgacta cgagctgtcc    2340
cgcggctaca tcgacgaaaa gatcctggag aaccagaaca tcatcaccca catgatcctg    2400
aactacgtcg gcagcgagga ctctgtgatc ccacgcatcc tgtacctgac ttggtactcc    2460
agcaacggag acatcaaggt cccttctacc aaggtgctgg ctatgatctc ttcagtcaag    2520
tcattcatgg aactgtcact gaggtccgtg aaggacagag aaaccatcat cagcgctgcc    2580
gagaagatcg ccgaggaact gaagatcgtc ccagaggaac tggtgcctct ggagggcaac    2640
ctgatgatca caacaagta cgctctgaag ttcttcccat tcgacaagca catcctggac    2700
aagctgccta ctctgatctc caactacatc gaagccgtca aggagggaaa gttcatgaac    2760
gtgaacatgc tggacaccta cgaaagcgtg cactcttttcc ctactgaaac cggactgccc    2820
ttcgtctaca ctttcaacgt gatcaagctg actaagacca gcggtaccgt ccaggctcag    2880
atcaaccctg acttcgcctt catcgtgaac tccaacctga ggctgacttt cagcaagaac    2940
gtccagggta gagtcggctt cgtgaccccc ttcgagcacc gccacttcat ctctggtatc    3000
gactcaaacc tgcacgtcta cgctcccctg aagatctccc tggacgtgaa cacccccaaag   3060 ggaaacatgc agtggaagat ctggcctatg aagggagagg aaaagtcaag actgttccac    3120
tactccgtgg tccccttcgt gagcaaccac gacatcctga acctgcgccc actgtccatg    3180
gaaaagggta ctcgtcccat gatcccagac gacaacacca gcctggcccct gcccaagaac   3240 gaaggcccat tccgcctgaa cgtcgagact gctaagacca cgaggaaat gtgggaactg    3300 atcgacactg agaagctgac cgacagactg ccataccctt ggaccatgga caacgagcgc    3360
tacgtgaagg tcgacatgta catgaacctg gagggcgaac agaaggaccc cgtcatcttc    3420
tctacttcat tcgactccaa ggtcatgact cgtccagaca ccgacagcga aaactggacc    3480
cctaagatga tggctgtgga gcccactgac aagcaggcca actctaagac caggagacag    3540
gaaatgatga gggaggctgg tagaggcatc gagtcagcca agtcctacgt ggtcgacgtg    3600
agagtccacg tgcccggaga gtccgaaagc gagactgtcc tgaccctggc ttggtctgaa    3660
tcaaacgtgg agtctaaggg aagactgctg ggattctgga gagtggaaat gccacgttca    3720
aacgccgact acgaggtctg catcggctca cagatcatgg tgtccccaga aaccctgctg    3780
tcctacgacg agaagatgga ccagaagcct aagatggact caacgtcga catccgttac    3840 ggaaagaact gcggaaaggg agagaggatc gacatgaacg gcaagctgcg ccagtccccct    3900 cgtctgaagg aactggtcgg cgctactagc atcatcaagg actgcgtgga ggacatgaag    3960
cgcggtaaca gatcctgcg tacctgccag aaggccgtgg tcctgtctat gctgctggac    4020
gaagtcgaca tcagcatgga ggtgccctct gacgctctga tcgccctgta ctcacaggga    4080
ctgttctccc tgagcgaaat cgacaacctg gacgtctccc tggacgtgag caacccaaag    4140
aacgctggca gaagaagat cgacgtgcgc gccaagctga acgagtacct ggacaaggct    4200
gacgtcatcg tgaacactcc tatcatggac gcccacttca aggacgtgaa gctgtcagac    4260
```

```
ttcggcttct ccactgaaga catcctggac accgctgacg aggacctgct gatcaacaac    4320
gtcttctacg aagacgaaac ctcctgcatg ctggacaaga ctcgtgccca gaccttcgac    4380
ggaaaggact accctctgag gctgggtcca tgctggcacg ctgtgatgac cacttaccct    4440
cgtatcaacc ccgacaacca caacgaaaag ctgcacatcc ctaaggacaa gtctgtctca    4500
gtgctgtcca gggaaaacga ggctggccag aaggaggtca aggtgctgct gggatctgac    4560
aagatcaagt tcgtgccagg taccacttca cagcctgaag tcttcgtgaa cggagagaag    4620
atcgtggtca gccgtaacaa ggcctaccag aaggtcgagg aaaacgaaat catcttcgag    4680
atctacaaga tgggtgaccg cttcatcggt ctgacttctg acaagttcga cgtctcactg    4740
gccctggacg gtgaacgcgt gatgctgaag gcttccgagg actacaggta cagcgtgaga    4800
ggactgtgcg gtaacttcga ccacgactcc accaacgact tcgtgggccc caagaactgc    4860
ctgttccgca agccagaaca cttcgtcgct agctacgccc tgatctctaa ccagtgcgag    4920
ggagactctc tgaacgtggc taagtcactg caggaccacg actgcatccg ccaggagcgt    4980
acccagcaga gaaacgtcat ctccgacagc gaatctggtc gcctggacac tgagatgtct    5040
acctggggct accaccacaa cgtcaacaag cactgcacta ccacagaac ccaggtgaag     5100
gaaactgacg acaagatctg cttcaccatg cgccccgtgg tcagctgcgc ttctggatgc    5160
actgccgtgg aaaccaagtc aaagccatac aagttccact gcatggaaaa gaacgaggct    5220
gccatgaagc tgaagaagcg tatcgagaag ggtgccaacc ccgacctgtc acagaagcca    5280
gtctccacca ctgaggaact gaccgtcccc ttcgtgtgca aggctcacca tcatcaccac    5340
caccaccact aatgaaagct t                                              5361
```

USE OF VITELLOGENIN FOR DEFINING AND TESTING NOVEL IMMUNOGENS IN INSECTS

CROSS-REFERENCE TO RELATED APPLICATIONS

This application is a U.S. 371 National Stage Application of PCT International Application No. PCT/US2021/048727, filed Sep. 1, 2021, which claims priority under 35 U.S.C. § 119 (e) to U.S. provisional application Ser. No. 63/074,365, filed Sep. 3, 2020, the content of each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Oct. 22, 2021, is named 121731-0710_SL.txt and is 23,110 bytes in size.

BACKGROUND

Vitellogenin (VTG or less popularly known as VG) is a precursor protein of egg yolk normally in the blood or hemolymph only of females that is used as a biomarker in vertebrates of exposure to environmental estrogens which stimulate elevated levels in males as well as females. The protein product of the gene is classified as a glycolipoprotein, having properties of a sugar, fat and protein. It is the precursor of the lipoproteins and phosphoproteins that make up most of the protein content of yolk.

Vitellogenin has been shown to bind to various proteins and transport them to ovaries in queen bees, where they are then passed on through eggs to newly hatched larvae. These proteins are capable of activating the non-specific insect immune mechanisms in insects, with the net result of a protective effect against pathogens, such as American foulbrood (AFB). American foulbrood (AFB) is a fatal bacterial disease of honey bee brood caused by the spore forming bacterium *Paenibacillus larvae*. It is not a stress related disease and can infect the strongest to the weakest colony in an apiary. Infected brood usually die at the pre-pupal or pupal stage. The disease is unable to be cured, meaning that destruction of infected colonies and hives or irradiation of infected material is the only current means to manage AFB. Thus a need exists in the art for therapeutic and preventive intervention. This disclosure satisfies this need and provides related advantages as well.

SUMMARY OF THE DISCLOSURE

Provided herein are novel solutions for the identification and measurement of these protective proteins to treat and prevent AFB.

To that end, this disclosure provides the methods and compositions for the identification, isolation, preparation and use of these protective proteins and fragments thereof.

In one aspect, the protection-inducing proteins an immunogenic fragments thereof from honey bee pathogens.

In one embodiment, provided herein is a method for identification of proteins. In one aspect, recombinant vitellogenin (rVg) is produced in an insect viral expression system, such as a baculovirus expression system. The rVg is bound to a sepharose CL column or other chromatographic support using cyanogen bromide or other covalent linking mechanism known to those skilled in the art. Alternatively, rVg may be bound to an ion exchange (IEX) column at favourable conditions (optimal pH, salt). Honey bee pathogens are inactivated and then solubilized so that internal and trans-membrane proteins are in solution. Suitable methods for inactivation include for example, sonication, followed by solubilization in non-ionic detergents such as Brij, Triton, octyl-glucoside and others known in the art. Honey bee pathogens are those responsible for American foulbrood, European foulbrood, deformed wing virus, varroa mite infestations and other viral, bacterial and parasitic diseases of honey bees. Solubilized protein mixtures of these pathogens are applied to the solid phase with rVg, and proteins that bind to rVg are eluted using a salt gradient and/or pH gradient. The rVg is covalently bound to the column and the proteins of interest are eluted. The rVg can be ionically bound to IEX gels, the rVg-protein mixture is eluted depending on binding characteristics, ionic strength, etc. Purified proteins or protein-rVg complexes are then identified using standard methods such as electrophoresis, HPLC, MS, etc.

In another aspect, provided herein is a proteomics method for the identification of antigenic proteins. In this method, rVg is used in the place of antibodies to detect protein in high throughput methods such as phage display, high throughput screening of the entire pathogen genome, and other methods known in the art. Labeled rVg or a polyclonal antibody is used to detect the proteins of interest, and then they may be further characterized. This method allows for the rapid screening of multiple disease agents extremely quickly.

In a yet further aspect, provided herein are vaccines and bacterins identified by these methods. After the proteins of interest are identified, they are partially sequenced, and the genes expressing such proteins are isolated, and the proteins are produced in a suitable eukaryotic or prokaryotic expression system (baculovirus, CHO, HEK, *E. coli, Saccharomyces*, and others known in the art). The recombinant proteins can be added to feed for queen bees as is described in U.S. Pat. No. 10,994,001, or may be introduced directly into hives in a suitable feed substance. Immunity in honey bees and larvae is generated and assessed as described in U.S. Pat. No. 10,994,001. Toll-like receptor (TLR) binding CpGs may be added to the vaccines or bacterins to enhance effector mechanisms.

Further provided is a novel test system for detecting and quantitating immunogens. Standard methods described and approved universally by regulatory bodies are indirect ELISA methods. In this method, 2 antibodies are used-one to trap the protein(s) of interest to a solid phase, and the second (usually a monoclonal) to detect the protein(s) of interest. The secondary antibody may be labeled with a fluorescent or enzyme label, and the specific binding quantified and compared to a standard. This novel method describes the use of rVg to detect immunogenic protein(s) of interest rather than a secondary antibody. The advantage of this method is that it would be detecting known immunogenic proteins, peptides, lids and polysaccharides rather than surrogate molecules that may or may not correlate with immunity.

DETAILED DESCRIPTION

Definitions

Figure 1:
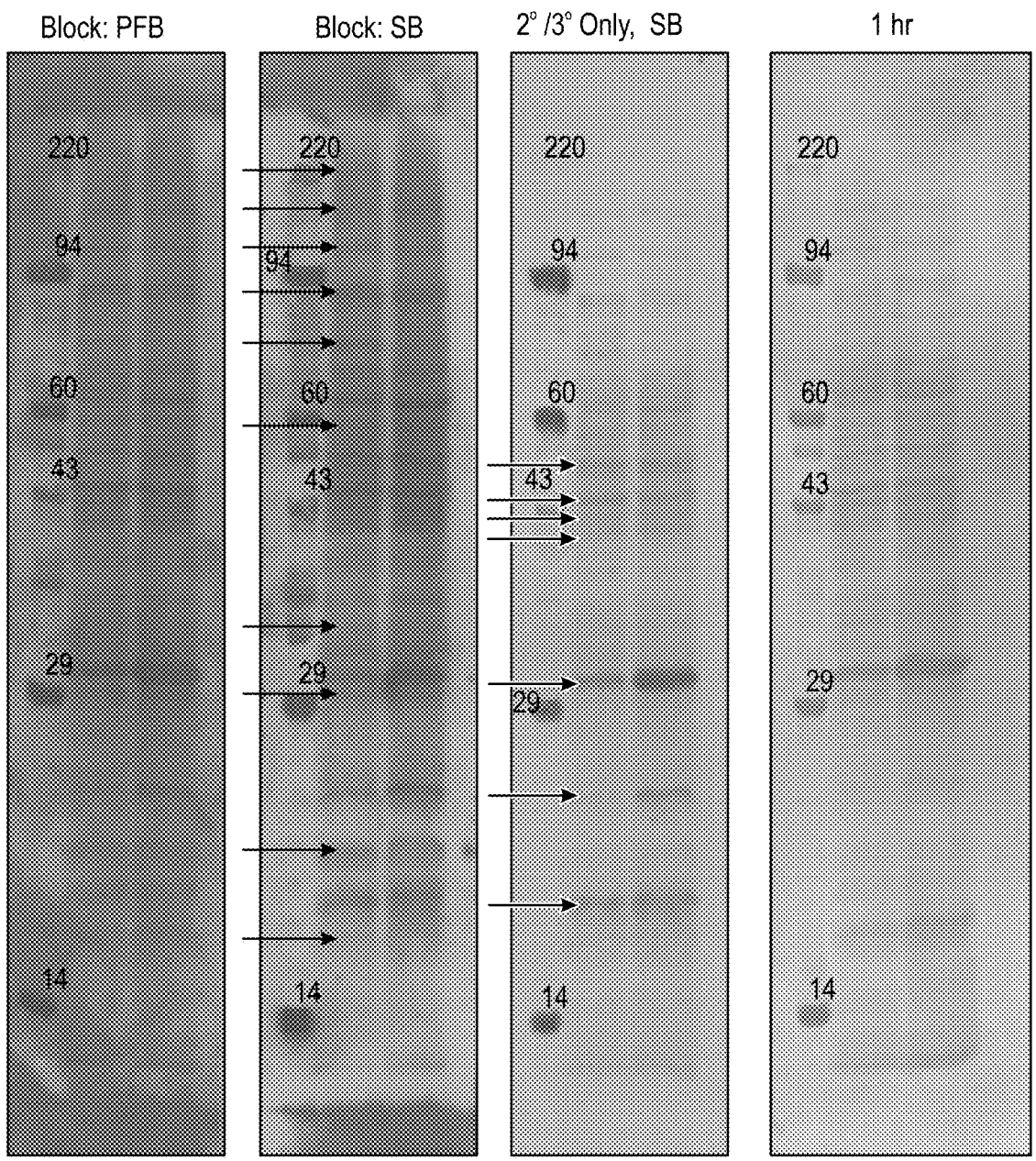
FIG. 1 shows a one dimensional gel using the below methods. 2 different blocking agents were assessed. Superblock was chosen as it appeared to provide a clearer image with less background staining. From Left to right: Vitellogenin blots with PF block, Vitellogenin blot with Superblock, Detection antibodies alone (i.e. anti-His tag and anti-mouse antibodies) and Coomassie stained (protein) gel.

As used herein and in the appended claims, singular articles such as "a" and "an" and "the" and similar referents in the context of describing the elements are to be construed to cover both the singular and the plural, unless otherwise indicated herein or clearly contradicted by context.

As used herein, "about" is understood by persons of ordinary skill in the art and may vary to some extent depending upon the context in which it is used. If there are uses of the term which are not clear to persons of ordinary skill in the art given the context in which the term "about" is used, "about" will mean up to plus or minus 10% of the particular term.

The term "exemplary" as used herein refers to "serving as an example, instance, or illustration," and not "preferred" or "advantageous over other embodiments."

Unless defined otherwise, technical and scientific terms used herein have the same meaning as commonly understood by a person of ordinary skill in the art. In particular, this disclosure utilizes routine techniques in the field of honeybee husbandry.

All numerical designations, e.g., pH, temperature, time, concentration, and molecular weight, including ranges, are approximations which are varied (+) or (−) by increments of 0.1 or 1 where appropriate. It is to be understood, although not always explicitly stated that all numerical designations are preceded by the term "about". The term "about" also includes the exact value "X" in addition to minor increments of "X" such as "X+0.1 or 1" or "X−0.1 or 1," where appropriate. It also is to be understood, although not always explicitly stated, that the reagents described herein are merely exemplary and that equivalents of such are known in the art.

As will be understood by one skilled in the art, for any and all purposes, all ranges disclosed herein also encompass any and all possible subranges and combinations of subranges thereof. Furthermore, as will be understood by one skilled in the art, a range includes each individual member.

As used in the specification and claims, the singular form "a", "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The term "isolated" as used herein with respect to cells, nucleic acids, such as DNA or RNA, refers to molecules separated from other DNAs or RNAs, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to cells or polypeptides which are isolated from other cellular proteins or tissues. Isolated polypeptides is meant to encompass both purified and recombinant polypeptides.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. Host cells can be prokaryotic or eukaryotic.

"Prokaryotic cells" that usually lack a nucleus or any other membrane-bound organelles and are divided into two domains, bacteria and archaea. In addition to chromosomal DNA, these cells can also contain genetic information in a circular loop called an episome. Bacterial cells are very small, roughly the size of an animal mitochondrion (about 1-2 µm in diameter and 10 µm long). Prokaryotic cells feature three major shapes: rod shaped, spherical, and spiral. Instead of going through elaborate replication processes like eukaryotes, bacterial cells divide by binary fission. Examples include but are not limited to *Bacillus* bacteria, *E. coli* bacterium, and *Salmonella* bacterium.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, bovine, porcine, murine, rat, avian, reptilian and human, e.g., HEK293 cells, Chinese Hamster Ovary (CHO) cells, CHO-S cells, CHO-K1 cells, 293T cells, HeLa cells, Baby hamster kidney (BHK) cells, and Sf9 cells. Sf9 cells are a clonal isolate of *Spodopter frugiperda*. They were originally isolated from ovarian tissue and are commonly used in insect cell culture for recombinant protein production using baculovirus. These cells are commercially available from American Type Culture Collection (ATCC) under CRL-1711.

DH10Bac can serve as a host for a recombinant pFastBac vector containing a cloned gene of interest. ThermoFisher Scientific provides these cells as MAX Efficiency DH10Bac Competent Cells. These DH10Bac cells harbor a baculovirus shuttle vector (bMON14272) and a helper plasmid (pMON7142), and are capable of supporting site-specific recombination between pFastBac and bMON14272 to generate high molecular weight bacmids that can then be amplified, purified, and used for insect cell transfection and subsequent gene expression. Kanamycin resistance for bacmid selection and maintenance is conferred by bMON14272, and tetracycline resistance by pMON7124. These cells are commercially available from ThermoFisher Scientific.

A baculovirus-insect expression system utilizes recombinant baculovirus (insect viruses) and their ability to manufacture high yields of biologically active proteins from insect cells. These systems are known in the art and commercially available. See, e.g., Jarvis, Baculovirus-insect cell expression systems, Methods Enzymol. (2009) 463:191-222; Scholz, J., Suppmann, S., A new single-step protocol for rapid baculovirus-driven protein production in insect cells. *BMC Biotechnol.* Vol. 17, 83 (2017); Lemaitre, R. P., et al., FlexiBAC: a versatile, open-source baculovirus vector system for protein expression, secretion, and proteolytic processing, BMC Biotechnol, Vol. 19, 20 (2019).

"ELISA" (enzyme-linked immunosorbent assay) is a plate-based assay technique designed for detecting and quantifying soluble substances such as peptides, proteins, antibodies, and hormones. Other names, such as enzyme immunoassay (EIA), are also used to describe the same technology. In the most simple form of an ELISA, antigens, e.g., antigens from the sample to be tested are attached to a surface. Then, a matching antibody is applied over the surface so it can bind the antigen. This antibody is linked to an enzyme and then any unbound antibodies are removed. In the final step, a substance containing the enzyme's substrate is added. If there was binding the subsequent reaction produces a detectable signal, most commonly a color change. Performing an ELISA involves at least one antibody with specificity for a particular antigen. The sample with an unknown amount of antigen is immobilized on a solid support (e.g, a polystyrene microtiter plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme or label or can itself be detected by a secondary antibody that is linked to an enzyme through bioconjugation. Between each step, the plate is typically washed with a mild detergent solution to remove any proteins or antibodies that are non-specifically bound. After the final wash step, the plate is developed by adding an enzymatic substrate to produce a signal, which indicates the quantity of antigen in the sample.

ELISA can also be performed in other forms of ligand binding assays. In one aspect, the technique essentially requires any ligating reagent that can be immobilized on the solid phase along with a detection reagent that will bind specifically and use an enzyme to generate a signal that can be properly quantified. In between the washes, only the ligand and its specific binding counterparts remain specifically bound or "immunosorbed" by antigen-antibody interactions or other interactions (protein-protein, e.g., Vitellogenin binding to a bee pathogen to the solid phase, while the nonspecific or unbound components are washed away.

"Amplify" "amplifying" or "amplification" of a polynucleotide sequence includes methods such as traditional cloning methodologies, PCR, ligation amplification (or ligase chain reaction, LCR) or other amplification methods. These methods are known and practiced in the art. See, e.g., U.S. Pat. Nos. 4,683,195 and 4,683,202 and Innis et al. (1990) Mol. Cell Biol. 10 (11): 5977-5982 (for PCR); and Wu et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting PCR are commercially available. Primers useful to amplify sequences from a particular region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

The term "genotype" refers to the specific allelic composition of an entire cell, a certain gene or a specific polynucleotide region of a genome, whereas the term "phenotype' refers to the detectable outward manifestations of a specific genotype.

As used herein, the term "gene" or "recombinant gene" refers to a nucleic acid molecule comprising an open reading frame and including at least one exon and (optionally) an intron sequence. A gene may also refer to a polymorphic or a mutant form or allele of a gene.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+

PIR. Biologically equivalent polynucleotides are those having the specified percent homology and encoding a polypeptide having the same or similar biological activity.

The term "an equivalent nucleic acid" refers to a nucleic acid having a nucleotide sequence having a certain degree of homology with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof.

The term "contacting" or interact" as used herein is meant to include detectable interactions between molecules, such as can be detected using, for example, a hybridization assay, an antibody binding assay such as ELIA. As such, the term interact or contacting is also meant to include "binding" interactions between molecules. Interactions may be, for example, protein-protein, protein-nucleic acid, or nucleic acid-nucleic acid in nature.

"Hybridization" refers to a reaction in which one or more polynucleotides react to form a hybridization complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

The term "mismatches" refers to hybridized nucleic acid duplexes which are not 100% homologous. The lack of total homology may be due to deletions, insertions, inversions, substitutions or frameshift mutations.

As used herein, the term "oligonucleotide" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or an RNA, the terms "adenosine", "cytidine", "guanosine", and "thymidine" are used. It is understood that if the nucleic acid is RNA, a nucleotide having a uracil base is uridine.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

As used herein, the term "carrier" encompasses any of the standard carriers, such as a phosphate buffered saline solution, buffers, water, and emulsions, such as an oil/water or water/oil emulsion, and various types of wetting agents. The compositions also can include stabilizers and preservatives. For examples of carriers, stabilizers and adjuvants, see Sambrook and Russell (2001), supra. Those skilled in the art will know many other suitable carriers for binding polynucleotides, or will be able to ascertain the same by use of routine experimentation. In one aspect of the invention, the carrier is a buffered solution such as, but not limited to, a PCR buffer solution.

A "gene delivery vehicle" is defined as any molecule that can carry inserted polynucleotides into a host cell. Examples of gene delivery vehicles are liposomes, biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection, sometimes called transduction), transfection, transformation or various other protein-based or lipid-based gene delivery complexes) as well as techniques facilitating the delivery of "naked" polynucleotides (such as electroporation, "gene gun" delivery and various other techniques used for the introduction of polynucleotides). Unless otherwise specified, the term transfected, transduced or transformed may be used interchangeably herein to indicate the presence of exogenous polynucleotides or the expressed polypeptide therefrom in a cell. The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

The term "express" refers to the production of a gene product. In some embodiments, the gene product is a polypeptide or protein. In some embodiments, the gene product is a mRNA, a tRNA, a rRNA, a miRNA, a dsRNA, or a siRNA.

A cell that "stably expresses" an exogenous polypeptide is one that continues to express a polypeptide encoded by an exogenous gene introduced into the cell either after replication if the cell is dividing or for longer than a day, up to about a week, up to about two weeks, up to three weeks, up to four weeks, for several weeks, up to a month, up to two months, up to three months, for several months, up to a year or more.

A "viral vector" is defined as a recombinantly produced virus or viral particle that comprises a polynucleotide to be delivered into a host cell, either in vivo, ex vivo or in vitro. Examples of viral vectors include retroviral vectors, lentiviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Ying, et al. (1999) Nat. Med. 5 (7): 823-827.

In aspects where gene transfer is mediated by a retroviral vector, a vector construct refers to the polynucleotide comprising the retroviral genome or part thereof, and a therapeutic gene. As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. Retroviruses carry their genetic information in the form of RNA; however, once the virus infects a cell, the RNA is reverse-transcribed into the DNA form which integrates into the genomic DNA of the infected cell. The integrated DNA form is called a provirus. As used herein, retroviral vector refers to a viral particle capable of introducing exogenous nucleic acid into a cell through a viral or viral-like entry mechanism. A "lentiviral vector" is a type of retroviral vector well-known in the art that has certain advantages in transducing nondividing cells as compared to other retroviral vectors. See, Trono D. (2002) Lentiviral vectors, New York: Spring-Verlag Berlin Heidelberg.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., International PCT Application No. WO 95/27071. Ads do not require integration into the host cell genome. Recombinant Ad derived vectors, particularly those that reduce the potential for recombination and generation of wild-type virus, have also been constructed. See, International PCT Application Nos. WO 95/00655 and WO 95/11984. Wild-type AAV has high infectivity and specificity integrating into the host cell's genome. See, Hermonat and Muzyczka (1984) Proc. Natl. Acad. Sci. USA 81:6466-6470 and Lebkowski, et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, CA) and Promega Biotech (Madison, WI). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

"Under transcriptional control" is a term well understood in the art and indicates that transcription of a polynucleotide sequence, usually a DNA sequence, depends on its being operatively linked to an element which contributes to the initiation of, or promotes, transcription. "Operatively linked" intends the polynucleotides are arranged in a manner that allows them to function in a cell.

A "probe" when used in the context of polynucleotide manipulation refers to an oligonucleotide that is provided as a reagent to detect a target potentially present in a sample of interest by hybridizing with the target. Usually, a probe will comprise a label or a means by which a label can be attached, either before or subsequent to the hybridization reaction. Suitable labels are described and exemplified herein.

A "primer" is a short polynucleotide, generally with a free 3' —OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in M. MacPherson et al. (1991) PCR: A Practical Approach, IRL Press at Oxford University Press. All processes of producing replicate copies of a polynucleotide, such as PCR or gene cloning, are collectively referred to herein as "replication." A primer can also be used as a probe in hybridization reactions, such as Southern or Northern blot analyses. Sambrook et al., supra. The primers may optionall contain detectable labels and are exemplified and described herein.

As used herein, the term "label" intends a directly or indirectly detectable compound or composition that is conjugated directly or indirectly to the composition to be detected, e.g., polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluoresecence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals (6th ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6th ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

Attachment of the fluorescent label may be either directly to the cellular component or compound or alternatively, can by via a linker. Suitable binding pairs for use in indirectly linking the fluorescent label to the intermediate include, but are not limited to, antigens/antibodies, e.g., rhodamine/anti-rhodamine, biotin/avidin and biotin/strepavidin.

The phrase "solid support" refers to non-aqueous surfaces such as "culture plates" "gene chips" or "microarrays." Such gene chips or microarrays can be used for diagnostic and therapeutic purposes by a number of techniques known to one of skill in the art. In one technique, oligonucleotides are attached and arrayed on a gene chip for determining the DNA sequence by the hybridization approach, such as that outlined in U.S. Pat. Nos. 6,025,136 and 6,018,041. The polynucleotides of this invention can be modified to probes, which in turn can be used for detection of a genetic sequence. Such techniques have been described, for example, in U.S. Pat. Nos. 5,968,740 and 5,858,659. A probe also can be attached or affixed to an electrode surface for the electrochemical detection of nucleic acid sequences such as described by Kayem et al. U.S. Pat. No. 5,952,172 and by Kelley et al. (1999) Nucleic Acids Res. 27:4830-4837.

Vitellogenin (Vg) is a precursor of egg yolk that transports protein and some lipid from the liver through the blood to the growing oocytes where it becomes part of the yolk. Normally, it is only found in the blood or hemolymph of females, and can therefore be used as a biomarker in vertebrates of exposure to environmental estrogens which stimulate elevated levels in males as well as females. "Vitellogenin" is a synonymous term for the gene and the expressed protein. The protein product is classified as a glycolipoprotein, having properties of a sugar, fat and protein. Vg polynucleotide and protein sequences can be found in UniProt database, and the sequences provided herein.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

An "artificial diet" intends a honey bee diet with an antigen or fragment thereof as described herein.

"Substantially homogeneous" describes a population of cells in which more than about 50%, or alternatively more than about 60%, or alternatively more than 70%, or alternatively more than 75%, or alternatively more than 80%, or alternatively more than 85%, or alternatively more than 90%, or alternatively, more than 95%, of the cells are of the same or similar phenotype. Phenotype can be determined by a pre-selected cell surface marker or other marker, e.g. myosin or actin or the expression of a gene or protein, e.g. a calcium handling protein, a t-tubule protein or alternatively, a calcium pump protein. In another aspects, the substantially homogenous population have a decreased (e.g., less than about 95%, or alternatively less than about 90%, or alternatively less than about 80%, or alternatively less than about 75%, or alternatively less than about 70%, or alternatively less than about 65%, or alternatively less than about 60%, or alternatively less than about 55%, or alternatively less than about 50%) of the normal level of expression than the wild-type counterpart cell or tissue.

The term "American foulbrood" or "American foulbrood disease" or "AFB" as used herein, refers to a fatal bacterial disease of honeybee brood caused by the spore forming bacterium *Paenibacillus larvae*. Since *Paenibacillus larvae* causes American fouldbrood disease in honeybees, *Paenibacillus larvae* is referred to herein as a "disease-causing" bacterium or a "disease species."

The terms "non-disease causing" species or "non-disease species" as used herein refer to species of bacteria which may or may not be pathogenic but which do not cause the disease being targeted. For example, with respect to American foulbrood disease which is caused by *Paenibacillus larvae*, exemplary non-disease *Paenibacillus* species, which may be found for example in the environment, but not on humans or in human wounds may include e.g., *Paenibacillus alvei, Paenibacillus dendritiformis Paenibacillus amylolyticus, Paenibacillus campinasensis, Paenibacillus chondroitinus, Paenibacillus chungangensis, Paenibacillus doosanensis, Paenibacillus glucanolyticus, Paenibacillus humicus, Paenibacillus lactis, Paenibacillus lautus, Paenibacillus lentimorbus, Paenibacillus maceran, Paenibacillus macerans*-like, *Paenibacillus macquariensis, Paenibacillus motobuensis, Paenibacillus pabuli, Paenibacillus phoenicis, Paenibacillus polymyxa, Paenibacillus popilliae, Paenibacillus puldeungensis, Paenibacillus residui, Paenibacillus stellife, Paenibacillus thiaminolyticus, Paenibacillus validus*, and *Paenibacillus xylanisolvens*. By way of example, *Paenibacillus alvei* and *Paenibacillus dendritiformis* are pathogenic and will inflict a brood disease on larvae but the disease is not American Foulbrood caused by *Paenibacillus larvae* and are thus non-disease forming species.

The term "honey bee" as used herein refers to is any bee which is a member of the genus *Apis*, primarily distinguished by the production and storage of honey and the construction of perennial, colonial nests from wax. For example, two species of honey bees, namely *A. mellifera* or *A. cerana* indica, are often maintained by beekeepers. Honey bees include but are not limited to *Apis andreniformis* and *Apis florea* in subgenus *Micrapis, Apis dorsata* in subgenus *Megapis*, and *Apis cerana, Apis koschevnikovi, Apis mellifera* and *Apis nigrocincta* in subgenus *Apis*.

The term "bee colony" or "honeybee colony" as used herein, refers to a social unit of bees, e.g., honeybees comprising a colony. The social unit can be of any system organization utilized by bees, which has the purpose of facilitating survival of the group or colony. Typically, a "bee colony" consists of several thousand bees that cooperate in nest building, food collection, and brood rearing. Each member of a "bee colony" has a definite task to perform, and it takes the combined efforts of the entire colony to survive and reproduce. A colony typically comprises a single queen, thousands of workers, and hundreds of drones during late spring and summer. Thus, a bee colony is a "population of honeybees."

Typically, a "honeybee colony" peaks from late spring to summer and reaches a low point in winter. The social structure of the colony is maintained by the queen and workers and depends on an effective system of communication. Domesticated honeybees are cultivated in "beehives" or "honeybee hives." Thus, the term "beehive" or "honeybee hive" refers to a structure that functions as a habitation for a colony of bees, e.g., a colony of honeybees.

As used herein, the term "honey bee" is any bee that is a member of the genus *Apis*. Two species of honey bees, *A. mellifer, A. cernan indica, A. andrreniformis, A. florea, A. koschevnikovie*, and *A. nigrocincta* are examples of such.

The term "nurse bee" as used herein intends are the bees that feed the worker larvae worker jelly that is secreted from glands that produce royal jelly.

The term "worker bee" as used herein intends any female (eusocial) bee that lacks the full reproductive capacity of the colony's queen bee.

The term "brood" intends the three developmental stages in bees, which are collectively known as brood. Bees begin in eggs, which hatch to become larvae (plural). The larvae is legless and is specialized to eat.

The term "prophylactic" or "vaccine" refers to an agent that acts to prevent a disease e.g., a honeybee disease, such as e.g., Foulbrood caused by the bacterium *Paenibacillus larvae* in the brood.

The term "vaccinate" as used herein, refers to means for producing immunity against a disease e.g., producing immunity to *Paenibacillus larvae*, so as to prevent a disease or condition from occurring (prophylactic treatment) or inhibiting the disease from spreading (slowing or arresting its development) in the brood, larvae, progeny or colony.

The term "treatment" intends to raise an immune response in the queen which is then passed on to her progeny.

The term "raise an immune response" intends that the treatment the vaccine or treatment produces the non-disease causing antigens in the ovaries of the honey bee queen or to the developing eggs.

An "antigen/unit" intends the number of cells or antigenic fragments of the non-disease pathogen.

The term "dose" intends the amount provided to the queen bee, the worker bee, nurse bee or larvae in one feeding or unit amount of food.

Modes for Carrying Out the Disclosure

Any composition prepared by or isolated from these methods are provided herein as well as use thereof in preventive and therapeutic methods.

Provided herein is a method to isolate a honey bee antigen that could be useful as a vaccine, the method comprising, or consisting essentially of, or yet further consisting of, contacting purified or recombinant vitellogenin (rVg) with a solid support under conditions to form rVg bound to the solid support; contacting a solubilized inactivated honey bee pathogen with the rVg bound to the solid support; and then eluting the inactivated honey bee pathogens from the solid support to isolate the honey bee antigen. As used herein, the term antigen intends complete or full length proteins and fragments thereof. As is apparent to the skilled artisan wash steps to remove unbound rVg and antigen can be added to the method.

In one aspect, the solid support is selected from a chromatographic support, a sepharose CL column (Pharmacia), or an ion exchange column. These are commercially available from BioRad, Pall Corp., Thermofischer and Pharmacia.

The solid support can be a Sepharose CL column or other chromatographic support using cyanogen bromide or other covalent linking mechanism known to those skilled in the art. Alternatively, rVg may be bound to an ion exchange (IEX) column at favourable conditions (optimal pH, salt). These methods are known in the art and will vary with the rVg and the solid support.

As noted above, solubilized protein mixtures of these pathogens are applied to the solid phase or antigens or fragment thereof with rVg, and proteins that bind to rVg are eluted using an appropriate method depending on the antigen and column. In one aspect, a salt gradient and/or pH gradient is used to elute the proteins bound to the rVg. The rVg is covalently bound to the column and the proteins of interest are eluted. In one aspect, the rVg can be ionically bound to ion exchange chromatography gels (IEX gels), the rVg-protein mixture is eluted depending on binding characteristics, ionic strength, etc. Purified proteins or protein-rVg complexes are then identified using standard methods such as electrophoresis, high performance liquid chromatography (HPLC), mass spectrometry (MS), and/or protein sequencing, etc.

After eluting the isolated antigens, the method can further comprise, or consist essentially of, or yet further consist of, determining the identity of the isolated inactivated honey bee pathogens. This can be accomplished by sequencing the antigens using well-known techniques that will determine the antigen and the polynucleotide encoding the antigen. In a further aspect, the isolated antigen is expressed in a recombinant cell system for expression and/or multiplication of the antigen.

Also provided herein is a method to isolate a honey bee antigen that could be useful as a vaccine, the method comprising, or consisting essentially of, or yet further consisting of, binding an anti-His tag or anti-Vg antibody with a solubilized inactivated honey bee pathogen and detecting any antibody bound to the inactivated honey bee pathogen, wherein the antibody or inactivated honey bee pathogen is detectably labeled.

In one aspect, the antibody or inactivated honey bee pathogen is detectably labeled. Such labels are known in the art and described herein. Anti-His tag antibodies are commercially available from Cell Signaling Technology, Invitrogen, ThermoFisher, and other commercial vendors. Anti-Vg antibodies are made using purified or rVg or fragments thereof using conventional techniques well-known in the art.

The rVg for use in the methods can be expressed in a prokaryotic or eukaryotic cell system, e.g., baculovirus, CHO, HEK, *E. coli, Saccharomyces*, and others known in the art. In one aspect, recombinant vitellogenin (rVg) is produced in an insect viral expression system, such as a baculovirus expression system. In one aspect, the baculovirus expression system is the DH10Bac system.

Any Vg protein or fragment can be used in the method. One non-limiting example is the rVg having the amino acid sequence of SEQ ID NO: 1, or a fragment or an equivalent thereof, with and without the His tag. The polynucleotide encoding SEQ ID NO: 1 is provided in SEQ ID NO: 2. When the His tag is not used, other detectable labels can be used, e.g., a radioisotope labels or a fluorescent label or, in the case of an enzymatic label, it may catalyze chemical alteration of a substrate compound or composition which is detectable. As such, suitable labels include, but are not limited to radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluoresecence assays, the detectable response can be generated directly using a luminophore or fluorophore associated with an assay component actually involved in binding, or indirectly using a luminophore or fluorophore associated with another (e.g., reporter or indicator) component.

Prior to contacting the honey bee pathogens (antigens and fragments thereof) with the solid support or antigen or fragment thereof, they are inactivated and then solubilized so that internal and trans-membrane proteins are in solution. Suitable methods for inactivation include for example, sonication, followed by solubilization in non-ionic detergents such as Brij, Triton, octyl-glucoside and others known in the art. The antigen contacted with the solid support can comprise one or multiple types of antigens, e.g., from the same or different pathogen.

Non-limiting examples of honey bee antigens for use in the method are those responsible for American foulbrood, European foulbrood, deformed wing virus, Varroa mite infestations and other viral, bacterial and parasitic diseases of honey bees. Examples of such include, without limitation, *Paenibacillus larvae, Paenibacillus alvei, Paenibacillus dendritiformis Paenibacillus amylolyticus, Paenibacillus campinasensis, Paenibacillus chondroitinuis, Paenibacillus chungangensis, Paenibacillus doosanensis, Paenibacillus glucanolyticus, Paenibacillus humicus, Paenibacillus lactis, Paenibacillus lautus, Paenibacillus lentimorbus, Paenibacillus maceran, Paenibacillus macerans*-like, *Paenibacillus macquariensis, Paenibacillus motobuensis, Paenibacillus pabuli, Paenibacillus phoenicis, Paenibacillus polymyxa, Paenibacillus popilliae, Paenibacillus puldeungensis, Paenibacillus residui, Paenibacillus stellife, Paenibacillus thiaminolyticus, Paenibacillus validus*, or *Paenibacillus xylanisolvens*. After isolation of the antigen or fragment thereof (e.g., eluting the isolated antigens) the methods can further comprise, or consist essentially of, or yet further consist of, determining the identity of the isolated inactivated honey bee pathogens. This can be accomplished by sequencing the antigens using well-known techniques that will determine the antigen and the polynucleotide encoding the antigen. In a further aspect, the isolated antigen is expressed in a recombinant cell system for expression and/or multiplication of the antigen.

In another aspect, provided herein is a proteomics method for the identification of antigenic proteins. In this method, rVg is used in the place of antibodies to detect protein in high throughput methods such as phage display, high throughput screening of the entire pathogen genome, and other methods known in the art. Labeled rVg or an anti-His tag antibodyis used to detect the proteins of interest, and then they may be further characterized. This method allows for the rapid screening of multiple disease agents extremely quickly.

In a yet further aspect, provided herein are vaccines and bacterins identified by these methods. After the proteins of interest are identified, they are partially sequenced, and the genes expressing such proteins are isolated, and the proteins are produced in a suitable eukaryotic or prokaryotic expression system (baculovirus, CHO, HEK, *E. coli, Saccharomyces*, and others known in the art). The recombinant proteins can be added to feed for queen bees as is described in U.S. Pat. No. 10,994,001, or may be introduced directly into hives in a suitable feed substance. Immunity in honey bees and larvae is generated and assessed as described in U.S. Pat. No. 10,994,001. Toll-like receptor (TLR) binding CpGs may be added to the vaccines or bacterins to enhance effector mechanisms.

In a specific embodiment, provided herein is a composition, comprising, or consisting essentially of, or yet further consisting of, the immunogenic proteins and a carrier. In one aspect, the composition comprises, or consisting essentially of, or yet further consisting of, the proteins or immunogenic fragments thereof and a carrier. A carrier can be a solid or a liquid carrier and can include preservatives, insect nutrients, or other coloring agents as necessary. In one specific embodiment, the carrier is an insect food, such as a queen bee wafer or sugar feed.

Compositions of the present invention are easily administered or fed to insects. In addition to bacteria, fungi, fragments and/or spores thereof, the edible composition may optionally comprise one or more acceptable (e.g. pharmaceutically acceptable) agents selected from the group consisting of carrier(s) (e.g. water, glucose or lactose), adjuvant(s), excipient(s), auxiliary excipient(s), anti-septic(s), stabilizing, thickening or coloring agent(s), perfume(s), binding agent(s), filling agent(s), lubricating agent(s), suspending agent(s), sweetener(s), flavoring agent(s), gelatinizer(s), anti-oxidant(s), preservative(s), buffer(s), pH regulator(s), wetting agent(s) and components normally found in corresponding products. However, in a very specific embodiment of the disclosure only bacteria, fungi, fragments thereof and/or spores thereof are needed in the composition. In a further specific embodiment the composition consists of only bacteria, fungi, fragments thereof and/or spores thereof and water.

In one specific embodiment of the invention, the compositions or artificial diet may be used for example in solid, semisolid or liquid form, such as in the form of patties, syrups, drenches, dustings, pastes, tablets, pellets, capsules, solutions, emulsions, suspensions or like. Preferably the composition is for oral administration.

As used herein, the term "prevent" or "preventing" refers to feeding or administration of microbes to an insect for purposes which include not only 100% or complete prevention but also partial prophylaxis and therefore also amelioration or alleviation of disorders or symptoms related to microbial infections. Preventive effect may be assessed e.g. by monitoring the symptoms mentioned in any of the tables of FIGS. 6-9 of U.S. Pat. No. 10,994,001, incorporated herein by reference. In this respect, the present disclosure can provide any amount of increase e.g. in the survival data compared to untreated controls.

In one aspect, the methods further comprise feeding a honey bee queen or worker bee an artificial insect diet comprising antigen or fragment thereof isolated by the above methods. The compositions are useful as vaccines. In one aspect, the amount of antigen in the artificial diet is 1 to 20% by weight. The artificial diet can be administered to the queen bee for administration one, two or three times a year. In one aspect, the honey bee queen prior is feed the artificial diet prior to egg laying. After consumption of the diet, the queen bee and/or the hive is challenged to determine protective or therapeutic response, as noted herein and U.S. Pat. No. 10,994,001, incorporated herein by reference.

Also provided herein is a method selected from: treating, raising an immune response or immunizing a honeybee larvae, honeybee, honeybee hatched from a treated queen bee, honeybee population or honeybee hive against AFB, the method comprising, or alternatively consisting essentially of, or yet further consisting essentially of, administering an effective amount of the composition as described herein to a nurse bees or the honeybee queen or honey bee larvae thereby treating, raising an immune response, or immunizing the queen bee and the honeybee larvae produced by the queen bee.

Experimental Methods

Preparation of Recombinant Vitellogenin. The recombinant vitellogenin was produced by Genscript, Inc. (Genscript, see https://www.genscript.com/?src=google&gclid=Cj0KCQjwvaeJBhCvARIsABgTDM419ret qScAAlyWup5xcTOXQC5muC904cZ7wSVpn9b62LHArb j7rqQaAvBZEALw_wcB, last accessed on Aug. 28, 2021) using their proprietary methods, vector technologies and expression systems. The target DNA sequence of honey bee VG was synthesized and then subcloned into a target vector for insect cell expression. The map of the construct is shown in FIG. 5. DH10Bac was used for the recombinant bacmid (rbacmid) generation. The positive rbacmid containing VG sequence gene was confirmed by polymerase chain reaction (PCR).

Virus Generation

Sf9 cells were grown in Sf-900 II SFM Expression Medium (Life Technologies, Catalog Number: 10902-088). The cells were maintained in Erlenmeyer Flasks at 27° C. in an orbital shaker. One day before transfection, the cells were seeded at an appropriate density in 6 wells CORNING-COSTAR. On the day of transfection, DNA and Transfection Reagent (PROMEGA, Catalog Number: E2691) were mixed at an optimal ratio and then added into the plate with cells ready for transfection. Cells were incubated in Sf-900 II SFM for 5-7 days at 27° C. before harvest. The supernatant was collected after centrifugation and designated as P1 viral stock. P2 was amplified for later infection. The expression was analyzed by Western blot.

Antigen Expression

The 0.5 L Sf9 cell culture were infected by Passage 2 virus. Cells were incubated in Sf-900II SFM (1×) for 3 days at 27° C. before harvest. The expression was analyzed by Western blot.

Purification and Analysis

Cell culture was centrifuged and followed by filtration. Filtered medium supernatant was incubated with Ni-NTA to capture the target protein. Higher purity fractions were pooled and followed by 0.22 μm filter sterilization. Proteins were analyzed by SDS-PAGE and Western blot by using standard protocols for molecular weight and purity measurements. The primary antibody for Western blot was Mouse-anti-His mAb (GenScript, Cat. No. A00186). The concentration was determined by Bradford protein assay with BSA as a standard.

Anti-His-tag Antibody

The anti-His antibody used was a monoclonal Mouse-anti-His antibody (GenScript, Cat. No. A00186).

*Paenibacillus larvae* Strain

*Paenibacillus larvae* strain was isolated from NY state bee hive. The strain has been tested found to be a pure strain of *Paenibacillus larvae* strain (99.4% similarity to *Paenibacillus larvae* strain DSM 7030) and found to be the ERIC I Pathotype.

Growth Medium

*P. larvae* strain was grown on enriched Mueller-Hinton MYPGP agar medium, for 2-6 days, harvested and then snap-frozen at −80° C. and shipped for protein analysis on dry ice, with a temperature control monitor, to avoid any proteolysis.

Analysis of *P. larvae* Vittellogenin Western Blot

Gel loading and sample preparation are given in Table 1 (see 2D gel analysis, below).

TABLE 1

| Gel ID # | Sample | μl loaded | μg loaded | Treatment |
|---|---|---|---|---|
| LF1473 #11 | bee hive isolate RL21-1404JUN21 | 150 | 400 | Coomassie |

TABLE 1-continued

| Gel ID # | Sample | μl loaded | μg loaded | Treatment |
|---|---|---|---|---|
| LF1473 #12 | bee hive isolate RL21-1404JUN21 | 150 | 400 | No Vitellogenin |
| LF 1473 #13 | bee hive isolate RL21-1404JUN21 | 150 | 400 | Vitellogenin |

2D Gel Loading and Sample Preparation.

The four cell pellet was lysed in 225 μl of Osmotic Lysis Buffer containing protease inhibitor stock, nuclease stock, and phosphatase inhibitor stocks (I and II), 75 μl SDS Boiling Buffer without β-mercaptoethanol, and 100 mg of washed glass beads (Sigma G9268, mesh size 425-6000 microns) as described by Jazwinski (SDS-polyacrylamide gel electrophoresis. Trends in Biochemical Science, 25, 590-592. Jazwinski, S. M. (1990)). The sample was vortexed 2 minutes, sonicated 15 minutes, vortexed again for 2 minutes, and placed in a dry bath at 95° C. for 10 minutes. The sample was centrifuged, and the supernatants was combined into one tube. The protein concentration (4.72 μg/μl) was then determined using the BCA assay (Smith et. al. Anal. Biochem. 150:76-85, 1985, and Pierce Chemical Co., Rockford, IL). The sample was then lyophilized, and redissolved to 2.66 mg/ml in 1:1 diluted SDS Boiling Buffer: Urea Sample Buffer before loading (see 2D gels below).

Electrophoresis and Western Blot

Two-dimensional electrophoresis was performed according to the carrier ampholine method of isoelectric focusing (O'Farrell, P. H., J. Biol. Chem. 250:4007-4021, 1975; Burgess-Cassler, A., Johansen, J., Santek, D., Ide J., and Kendrick N., Clin. Chem. 35:2297, 1989; Kendrick, N., C. C. Darie, M. Hoelter, G. Powers, and J. Johansen, Adv Exp Med Biol, 2019. 1140: p. 563-574). Isoelectric focusing was carried out in a glass tube of inner diameter 3.3 mm using 2.0% 4-8 mix (Serva, Heidelberg, Germany) for 20,000 volt-hrs. One μg of an IEF internal standard, tropomyosin, was added to each sample. This protein migrates as a doublet with lower polypeptide spot of MW 33,000 and μl 5.2; an arrow on the stained gels marks its position. The enclosed tube gel pH gradient plot for this set of Servalytes was determined with a surface pH electrode.

After equilibration for 10 min in buffer "O" (10% glycerol, 50 mM dithiothreitol, 2.3% SDS and 0.0625 M tris, pH 6.8), each tube gel was sealed to the top of a stacking gel that overlaid a 10% acrylamide slab gel (1.0 mm thick). SDS slab gel electrophoresis was carried out for about 5 hrs at 25 mA/gel. The following proteins (MilliporeSigma) were used as molecular weight standards: myosin (220,000), phosphorylase A (94,000), catalase (60,000), actin (43,000), carbonic anhydrase (29,000), and lysozyme (14,000). These standards appear as bands at the basic edge of the Coomassie Brilliant Blue R-250 stained 10% acrylamide slab gel. The gel was dried between sheets of cellophane paper with the acid edge to the left.

After slab gel electrophoresis, duplicate gels for blotting were placed in transfer buffer (10 mM CAPS, pH 11.0, 10% MeOH) and transblotted onto PVDF membrane overnight at 225 mA and approximately 100 volts/two gels. The same proteins as above (MilliporeSigma) were used as molecular weight standards. These standards appear as bands at the basic edge of the Coomassie Brilliant Blue R-250-stained membrane.

Western Blot Methods

The blots were destained in 100% methanol and rinsed briefly in Tween-20 tris buffer saline (TTBS).

His Tag & Anti-Mouse IgG-HRP Only (No Vitellogenin), Super Block, LF1473 #12 (See 2D gels, in the Figures).

The blot was blocked overnight in Super Block (ThermoFisher, Cat #37535) containing 0.05% Tween-20 (SBT). The blot was then placed in secondary solution (THE His Tag [GenScript, Cat #A00186-100, Lot #17K001367] diluted to 0.02 μg/ml in SBT) for two hours and rinsed 3×10 minutes in TTBS. The blot was then placed in tertiary antibody (anti-Mouse IgG-HRP [GE, Cat #NA931V, Lot #17205275] diluted 1:2,000 in SBT) for two hours, rinsed as above, treated with ECL, and exposed to x-ray Vitellogenin, Super Block, LF1473 #13 (See 2Dgels, Below)

The blot was blocked for two hours in Superblock (Thermofischer) containing 0.05M Tris buffer, pH 6.8 (SBT). The blot was then incubated overnight in primary solution (Vitellogenin (GenScript, Lot #U5329GB010-3/P4GE001)) diluted to 0.1 μg/ml in SBT) and rinsed 3×10 minutes in TTBS. The blot was then placed in secondary solution (THE His Tag [GenScript, Cat #A00186-100, Lot #17K001367] diluted to 0.02 μg/ml in SBT) for two hours and rinsed 3×10 minutes in TTBS. The blot was then placed in tertiary antibody (anti-Mouse IgG-HRP [GE, Cat #NA931V, Lot #17205275] diluted 1:2,000 in SBT) for two hours, rinsed as above, treated with ECL, and exposed to x-ray film.

Experimental Results

Figure 2:
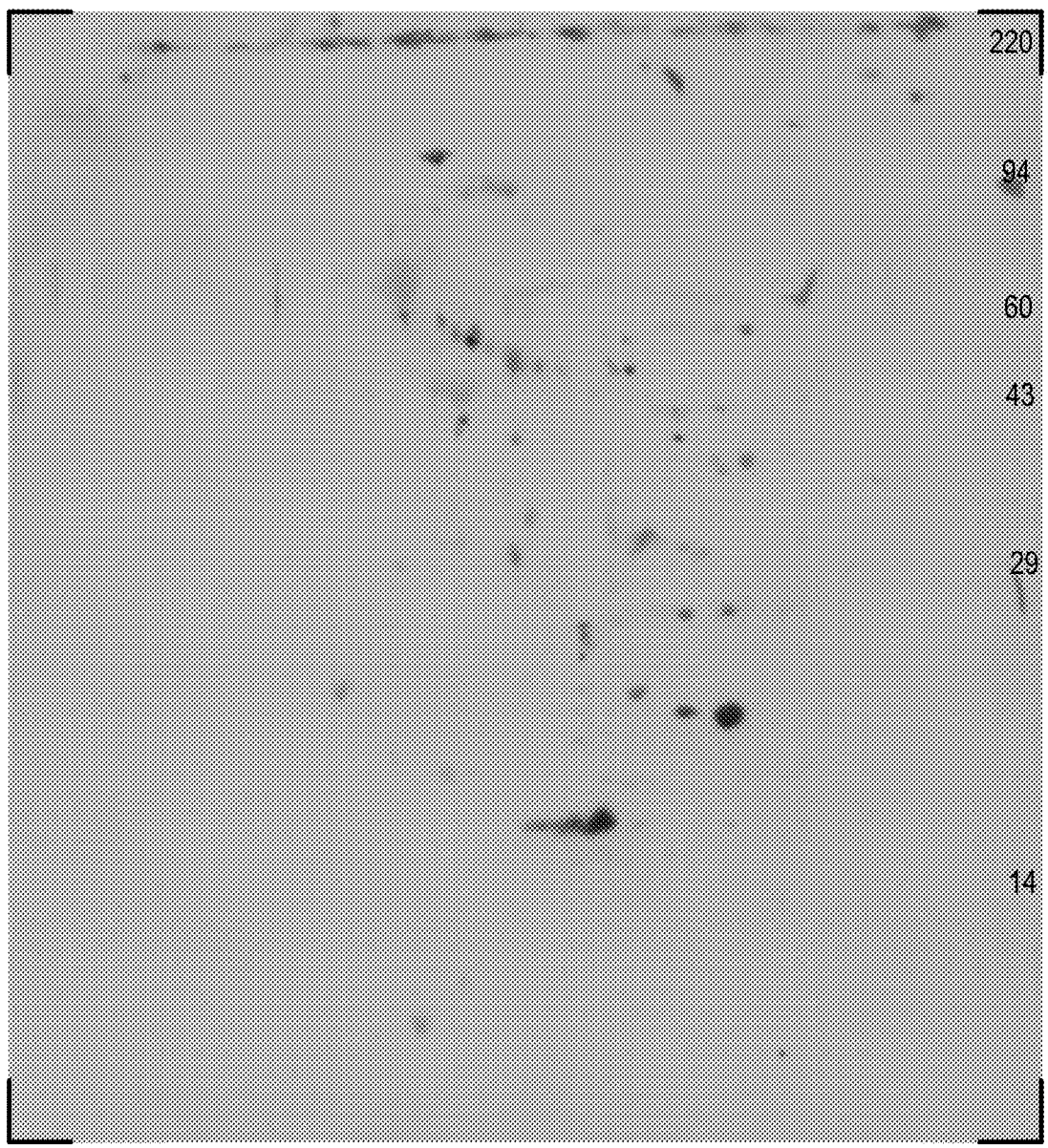
FIG. 2 shows a two dimensional gel. Methods are described below. 2D pattern following staining with detection antibodies only (no vitellogenin).

FIG. 2 shows the construct of the one dimensional electrophoresis.

The 1D (molecular weight) gel analysis indicated that there were a number of proteins that may bind specifically to Vitellogenin. These were initially identified by the red arrows in FIG. 1. Proteins that bound non-specifically to the either the His-tag or anti-mouse Ig antibodies are indicated by yellow arrows. These data led to analysis using 2D gels.

2D Gel Analysis.

Figure 3:
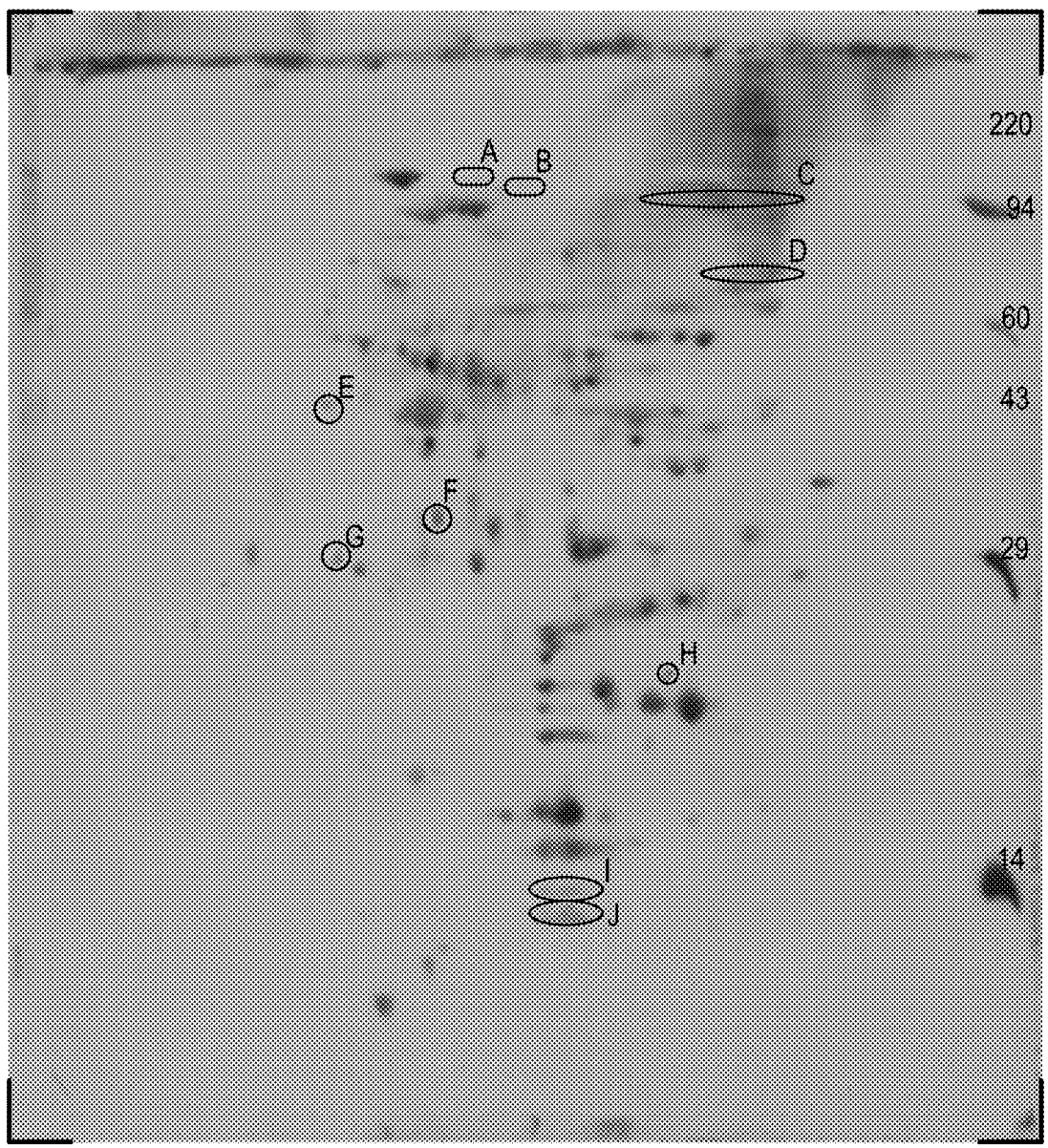
FIG. 3 shows a 2D gel pattern following staining with vitellogenin and detection antibodies. The circled spots are those that were detected uniquely by vitellogenin, i.e. did not bind to either of the detection antibodies.
Figures 4, 5:
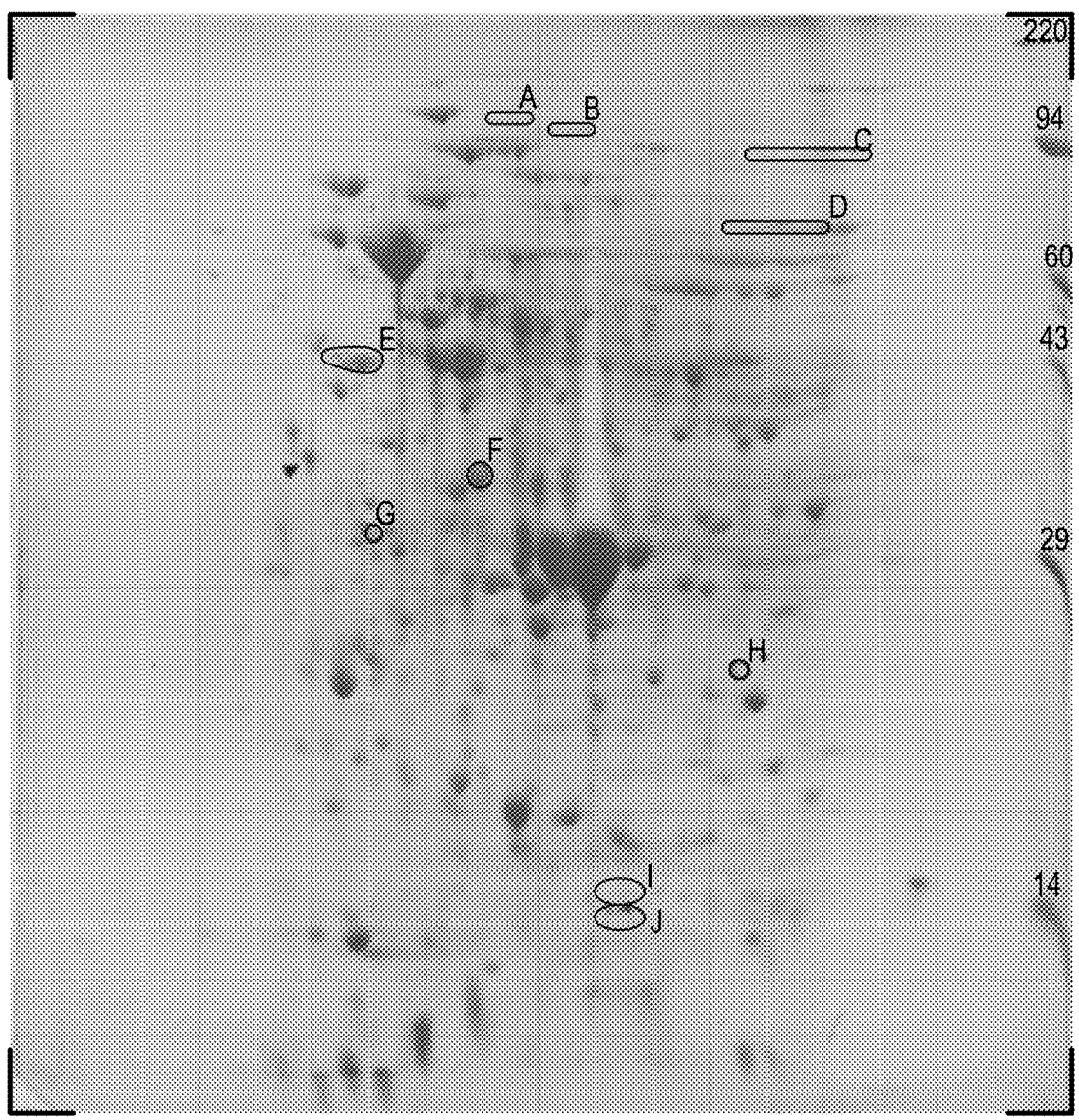
FIG. 4 is a Coomassie stained gel indicating the proteins detected by specific vitellogenin staining.
FIG. 5 shows a map of an exemplary recombinant vitellogenin construct.

FIG. 2 and FIG. 3 indicate the results of detection of protein binding by vitellogenin. Using simple visual overlay at least 10 spots can be detected that bind uniquely to vitellogenin. In FIG. 4, these are identified on the Coomassie stained gel.

Experimental Discussion

Non-Specific Binding

It appears that there is a considerable amount of non-specific binding-either by the anti-HIS tag or by the anti-HRP. Low level non-specific binding appeared to be at a MW~35-50, with stronger signals at MW between 14 and 29.

rVg Specific Binding

Honeybee rVG binds specifically to multiple proteins detected. It is noteworthy that there are some proteins that appear in very small concentrations, show a high degree of binding (e.g. H, I, J in the 2D gels above). These tended to be lower MW proteins between 14 and 29 MW. There also appears to be a stronger signal at ~60 and 94 MW and between 94 and 220 MW.

Virulence Factors of PL

Known virulence factors for *P. larvae* include enolase (MW 82-200 kDa, depending on isoform), and a chitinase (49 kDa). A variety of toxins have also been proposed as virulence factors, such as C3 mART which has a MW between 20 and 25 kDa. Further analysis of the proteins bound by vitellogenin will identify those proteins that are involved in immunity.

EQUIVALENTS

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

It should be understood that although the present disclosure has been specifically disclosed by specific embodiments and optional features, modification, improvement and variation of the embodiments therein herein disclosed may be resorted to by those skilled in the art, and that such modifications, improvements and variations are considered to be within the scope of this disclosure. The materials, methods, and examples provided here are representative of particular embodiments, are exemplary, and are not intended as limitations on the scope of the disclosure.

The scope of the disclosure has been described broadly and generically herein. Each of the narrower species and subgeneric groupings falling within the generic disclosure also form part of the disclosure. This includes the generic description with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

```
Protein sequence of Vg
>U2111FG010-1 (Vitellogenin, C-His, His tag is underlined,
which is an optional element for the protein)
Protein Length = 1778 MW = 202109.1 Predicted pI = 6.82
                                                        SEQ ID NO: 1
MLLLLTLLLFAGTVAADFQHNWQVGNEYTYLVRSRTLTSLGDLSDVHTGILIKALL

TVQAKDSNVLAAKVWNGQYARVQQSMPDGWETE

ISDQMLELRDLPISGKPFQIRMKHGLIRDLIVDRDVPTWEVNILKSIVGQLQVDTQGE

NAVKVNSVQVPTDDEPYASFKAMEDSVGGKC

EVLYDIAPLSDFVIHRSPELVPMPTLKGDGRHMEVIKIKNFDNCDQRINYHFGMTDN

SRLEPGTNKNGKFFSRSSTSRIVISESLKHFT

IQSSVTTSKMMVSPRLYDRQNGLVLSRMNLTLAKMEKTSKPLPMVDNPESTGNLV

YIYNNPFSDVEERRVSKTAMNSNQIVSDNSLSSS

EEKLKQDILNLRTDISSSSSSISSSEENDFWQPKPTLEDAPQNSLLPNFVGYKGKHIG

KSGKVDVINAAKELIFQIANELEDASNIPVH

ATLEKFMILCNLMRTMNRKQISELESNMQISPNELKPNDKSQVIKQNTWTVFRDAIT

QTGTGPAFLTIKEWIERGTTKSMEAANIMSKL

PKTVRTPTDSYIRSFFELLQNPKVSNEQFLNTAATLSFCEMIHNAQVNKRSIHNNYP

VHTFGRLTSKHDNSLYDEYIPFLERELRKAHQ

EKDSPRIQTYIMALGMIGEPKILSVFEPYLEGKQQMTVFQRTLMVGSLGKLTETNPK

LARSVLYKIYLNTMESHEVRCTAVFLLMKTNP

PLSMLQRMAEFTKLDTNRQVNSAVKSTIQSLMKLKSPEWKDLAKKARSVNHLLTH

HEYDYELSRGYIDEKILENQNIITHMILNYVGSE

DSVIPRILYLTWYSSNGDIKVPSTKVLAMISSVKSFMELSLRSVKDRETIISAAEKIAE

ELKIVPEELVPLEGNLMINNKYALKFFPFD

KHILDKLPTLISNYIEAVKEGKFMNVNMLDTYESVHSFPTETGLPFVYTFNVIKLTK

TSGTVQAQINPDFAFIVNSNLRLTFSKNVQGR

VGFVTPFEHRHFISGIDSNLHVYAPLKISLDVNTPKGNMQWKIWPMKGEEKSRLFH

YSVVPFVSNHDILNLRPLSMEKGTRPMIPDDNT

SLALPKNEGPFRLNVETAKTNEEMWELIDTEKLTDRLPYPWTMDNERYVKVDMY

MNLEGEQKDPVIFSTSFDSKVMTRPDTDSENWTPK
```

-continued

MMAVEPTDKQANSKTRRQEMMREAGRGIESAKSYVVDVRVHVPGESESETVLTL

AWSESNVESKGRLLGFWRVEMPRSNADYEVCIGSQ

IMVSPETLLSYDEKMDQKPKMDFNVDIRYGKNCGKGERIDMNGKLRQSPRLKELV

GATSIIKDCVEDMKRGNKILRTCQKAVVLSMLLD

EVDISMEVPSDALIALYSQGLFSLSEIDNLDVSLDVSNPKNAGKKKIDVRAKLNEYL

DKADVIVNTPIMDAHFKDVKLSDFGFSTEDIL

DTADEDLLINNVFYEDETSCMLDKTRAQTFDGKDYPLRLGPCWHAVMTTYPRINP

DNHNEKLHIPKDKSVSVLSRENEAGQKEVKVLLG

SDKIKFVPGTTSQPEVFVNGEKIVVSRNKAYQKVEENEIIFEIYKMGDRFIGLTSDKF

DVSLALDGERVMLKASEDYRYSVRGLCGNFD

HDSTNDFVGPKNCLFRKPEHFVASYALISNQCEGDSLNVAKSLQDHDCIRQERTQQ

RNVISDSESGRLDTEMSTWGYHHNVNKHCTIHR

TQVKETDDKICFTMRPVVSCASGCTAVETKSKPYKFHCMEKNEAAMKLKKRIEKG

ANPDLSQKPVSTTEELTVPFVCKAHHHHHHHH**

DNA Sequence Encoding Vg (Signal Peptide is underlined
and is an optional element for the DNA Sequence).

SEQ ID NO: 2

<u>GAATTCGCCGCCACC</u>ATGCTGCTGCTGACTCTGCTGCTGTTCGCTGGTACCG

TGGCTGCCGACTTCCAGCACAACTGGCAGG

TCGGCAACGAGTACACCTACCTGGTGCGCTCTCGTACCCTGACTTCACTGGGCG

ACCTGTCCGACGTCCACACTGGAATCCTGAT

CAAGGCTCTGCTGACCGTGCAGGCCAAGGACTCTAACGTCCTGGCTGCCAAAGT

GTGGAACGGCCAGTACGCTCGTGTGCAGCAG

TCCATGCCCGACGGATGGGAGACTGAAATCAGCGACCAGATGCTGGAACTGCG

TGACCTGCCAATCTCAGGCAAGCCTTTCCAGA

TCAGGATGAAGCACGGACTGATCAGGGACCTGATCGTCGACAGAGACGTGCCA

ACCTGGGAGGTGAACATCCTGAAGTCTATCGT

CGGTCAGCTGCAGGTGGACACTCAGGGCGAAAACGCTGTGAAGGTCAACTCAG

TCCAGGTCCCCACCGACGACGAGCCATACGCT

TCCTTCAAGGCCATGGAAGACAGCGTCGGTGGCAAGTGCGAGGTGCTGTACGA

CATCGCCCCTCTGTCTGACTTCGTCATCCACC

GTTCACCCGAACTGGTGCCAATGCCTACCCTGAAGGGAGACGGTAGGCACATG

GAGGTCATCAAGATCAAGAACTTCGACAACTG

CGACCAGAGAATCAACTACCACTTCGGTATGACTGACAACAGCCGCCTGGAAC

CAGGTACCAACAAGAACGGCAAGTTCTTCAGC

CGCTCCAGCACTTCTCGTATCGTGATCTCCGAGAGCCTGAAGCACTTCACCATC

CAATCTTCAGTCACCACTTCAAAGATGATGG

TGTCCCCTAGGCTGTACGACAGACAGAACGGTCTGGTCCTGTCCCGTATGAACC

TGACTCTGGCTAAGATGGAAAAGACCTCTAA

GCCCCTGCCAATGGTCGACAACCCTGAGTCAACTGGCAACCTGGTGTACATCTA

CAACAACCCCTTCAGCGACGTCGAGGAACGC

CGTGTGAGCAAGACCGCCATGAACTCTAACCAGATCGTGTCAGACAACTCCCTG

-continued

```
TCCAGCTCTGAGGAAAAGCTGAAACAGGACA

TCCTGAACCTGAGGACTGACATCTCATCCAGCTCTTCATCCATCAGCTCTTCAGA

GGAAAACGACTTCTGGCAGCCTAAGCCCAC

CCTGGAGGACGCTCCACAGAACTCCCTGCTGCCTAACTTCGTGGGCTACAAGGG

AAAGCACATCGGCAAGAGCGGCAAGGTGGAC

GTCATCAACGCTGCCAAGGAACTGATCTTCCAGATCGCTAACGAACTGGAAGA

CGCCTCCAACATCCCAGTCCACGCCACTCTGG

AGAAGTTCATGATCCTGTGCAACCTGATGCGCACCATGAACCGTAAGCAGATCT

CAGAGCTGGAATCCAACATGCAGATCTCTCC

TAACGAACTGAAGCCCAACGACAAGTCACAGGTCATCAAGCAGAACACCTGGA

CTGTGTTCAGAGACGCTATCACCCAGACTGGC

ACCGGACCTGCCTTCCTGACTATCAAGGAATGGATCGAGCGCGGTACCACTAAG

TCTATGGAGGCTGCCAACATCATGTCAAAGC

TGCCCAAGACCGTGAGGACTCCAACCGACAGCTACATCAGATCTTTCTTCGAAC

TGCTGCAGAACCCTAAGGTGTCCAACGAGCA

GTTCCTGAACACTGCTGCCACCCTGAGCTTCTGCGAGATGATCCACAACGCTCA

GGTCAACAAGAGAAGCATCCACAACAACTAC

CCCGTGCACACTTTCGGCCGCCTGACCAGCAAGCACGACAACTCTCTGTACGAC

GAATACATCCCTTTCCTGGAGAGGGAACTGA

GAAAGGCCCACCAGGAGAAGGACTCCCCCCGTATCCAGACCTACATCATGGCT

CTGGGAATGATCGGTGAACCAAAGATCCTGAG

CGTGTTCGAACCTTACCTGGAGGGAAAGCAGCAGATGACTGTCTTCCAGAGGA

CCCTGATGGTGGGCTCTCTGGGAAAGCTGACT

GAAACCAACCCCAAGCTGGCCCGTTCTGTCCTGTACAAGATCTACCTGAACACT

ATGGAATCACACGAGGTCAGGTGCACTGCTG

TGTTCCTGCTGATGAAGACCAACCCTCCCCTGTCAATGCTGCAGCGTATGGCCG

AGTTCACTAAGCTGGACACCAACAGGCAGGT

CAACTCAGCTGTGAAGTCCACCATCCAGAGCCTGATGAAGCTGAAGTCCCCAG

AGTGGAAGGACCTGGCTAAGAAGGCCAGAAGC

GTGAACCACCTGCTGACTCACCACGAATACGACTACGAGCTGTCCCGCGGCTAC

ATCGACGAAAAGATCCTGGAGAACCAGAACA

TCATCACCCACATGATCCTGAACTACGTCGGCAGCGAGGACTCTGTGATCCCAC

GCATCCTGTACCTGACTTGGTACTCCAGCAA

CGGAGACATCAAGGTCCCTTCTACCAAGGTGCTGGCTATGATCTCTTCAGTCAA

GTCATTCATGGAACTGTCACTGAGGTCCGTG

AAGGACAGAGAAACCATCATCAGCGCTGCCGAGAAGATCGCCGAGGAACTGAA

GATCGTCCCAGAGGAACTGGTGCCTCTGGAGG

GCAACCTGATGATCAACAACAAGTACGCTCTGAAGTTCTTCCCATTCGACAAGC

ACATCCTGGACAAGCTGCCTACTCTGATCTC

CAACTACATCGAAGCCGTCAAGGAGGGAAAGTTCATGAACGTGAACATGCTGG

ACACCTACGAAAGCGTGCACTCTTTCCCTACT
```

-continued

```
GAAACCGGACTGCCCTTCGTCTACACTTTCAACGTGATCAAGCTGACTAAGACC

AGCGGTACCGTCCAGGCTCAGATCAACCCTG

ACTTCGCCTTCATCGTGAACTCCAACCTGAGGCTGACTTTCAGCAAGAACGTCC

AGGGTAGAGTCGGCTTCGTGACCCCCTTCGA

GCACCGCCACTTCATCTCTGGTATCGACTCAAACCTGCACGTCTACGCTCCCCTG

AAGATCTCCCTGGACGTGAACACCCCAAAG

GGAAACATGCAGTGGAAGATCTGGCCTATGAAGGGAGAGGAAAAGTCAAGACT

GTTCCACTACTCCGTGGTCCCCTTCGTGAGCA

ACCACGACATCCTGAACCTGCGCCCACTGTCCATGGAAAAGGGTACTCGTCCCA

TGATCCCAGACGACAACACCAGCCTGGCCCT

GCCCAAGAACGAAGGCCCATTCCGCCTGAACGTCGAGACTGCTAAGACCAACG

AGGAAATGTGGGAACTGATCGACACTGAGAAG

CTGACCGACAGACTGCCATACCCTTGGACCATGGACAACGAGCGCTACGTGAA

GGTCGACATGTACATGAACCTGGAGGGCGAAC

AGAAGGACCCCGTCATCTTCTCTACTTCATTCGACTCCAAGGTCATGACTCGTCC

AGACACCGACAGCGAAAACTGGACCCCTAA

GATGATGGCTGTGGAGCCCACTGACAAGCAGGCCAACTCTAAGACCAGGAGAC

AGGAAATGATGAGGGAGGCTGGTAGAGGCATC

GAGTCAGCCAAGTCCTACGTGGTCGACGTGAGAGTCCACGTGCCCGGAGAGTC

CGAAAGCGAGACTGTCCTGACCCTGGCTTGGT

CTGAATCAAACGTGGAGTCTAAGGGAAGACTGCTGGGATTCTGGAGAGTGGAA

ATGCCACGTTCAAACGCCGACTACGAGGTCTG

CATCGGCTCACAGATCATGGTGTCCCCAGAAACCCTGCTGTCCTACGACGAGAA

GATGGACCAGAAGCCTAAGATGGACTTCAAC

GTCGACATCCGTTACGGAAAGAACTGCGGAAAGGGAGAGAGGATCGACATGAA

CGGCAAGCTGCGCCAGTCCCCTCGTCTGAAGG

AACTGGTCGGCGCTACTAGCATCATCAAGGACTGCGTGGAGGACATGAAGCGC

GGTAACAAGATCCTGCGTACCTGCCAGAAGGC

CGTGGTCCTGTCTATGCTGCTGGACGAAGTCGACATCAGCATGGAGGTGCCCTC

TGACGCTCTGATCGCCCTGTACTCACAGGGA

CTGTTCTCCCTGAGCGAAATCGACAACCTGGACGTCTCCCTGGACGTGAGCAAC

CCAAAGAACGCTGGCAAGAAGAAGATCGACG

TGCGCGCCAAGCTGAACGAGTACCTGGACAAGGCTGACGTCATCGTGAACACT

CCTATCATGGACGCCCACTTCAAGGACGTGAA

GCTGTCAGACTTCGGCTTCTCCACTGAAGACATCCTGGACACCGCTGACGAGGA

CCTGCTGATCAACAACGTCTTCTACGAAGAC

GAAACCTCCTGCATGCTGGACAAGACTCGTGCCCAGACCTTCGACGGAAAGGA

CTACCCTCTGAGGCTGGGTCCATGCTGGCACG

CTGTGATGACCACTTACCCTCGTATCAACCCCGACAACCACAACGAAAAGCTGC

ACATCCCTAAGGACAAGTCTGTCTCAGTGCT
```

-continued

GTCCAGGGAAAACGAGGCTGGCCAGAAGGAGGTCAAGGTGCTGCTGGGATCTG

ACAAGATCAAGTTCGTGCCAGGTACCACTTCA

CAGCCTGAAGTCTTCGTGAACGGAGAGAAGATCGTGGTCAGCCGTAACAAGGC

CTACCAGAAGGTCGAGGAAAACGAAATCATCT

TCGAGATCTACAAGATGGGTGACCGCTTCATCGGTCTGACTTCTGACAAGTTCG

ACGTCTCACTGGCCCTGGACGGTGAACGCGT

GATGCTGAAGGCTTCCGAGGACTACAGGTACAGCGTGAGAGGACTGTGCGGTA

ACTTCGACCACGACTCCACCAACGACTTCGTG

GGCCCCAAGAACTGCCTGTTCCGCAAGCCAGAACACTTCGTCGCTAGCTACGCC

CTGATCTCTAACCAGTGCGAGGGAGACTCTC

TGAACGTGGCTAAGTCACTGCAGGACCACGACTGCATCCGCCAGGAGCGTACC

CAGCAGAGAAACGTCATCTCCGACAGCGAATC

TGGTCGCCTGGACACTGAGATGTCTACCTGGGGCTACCACCACAACGTCAACAA

GCACTGCACTATCCACAGAACCCAGGTGAAG

GAAACTGACGACAAGATCTGCTTCACCATGCGCCCCGTGGTCAGCTGCGCTTCT

GGATGCACTGCCGTGGAAACCAAGTCAAAGC

CATACAAGTTCCACTGCATGGAAAAGAACGAGGCTGCCATGAAGCTGAAGAAG

CGTATCGAGAAGGGTGCCAACCCCGACCTGTC

ACAGAAGCCAGTCTCCACCACTGAGGAACTGACCGTCCCCTTCGTGTGCAAGGC

TCACCATCATCACCACCACCACCACTAATGAAAGCTT

---

What is claimed is:

1. A method to isolate a honey bee antigen comprising:
   contacting recombinant vitellogenin (rVg) with a solid support to form rVg to the solid support;
   contacting a solubilized inactivated honey bee pathogen with the rVg bound to the solid support; and
   eluting the inactivated honey bee pathogen to isolate the honey bee antigen.

2. The method of claim 1, further comprising determining the identity of the isolated inactivated honey bee pathogen.

3. The method of claim 2, wherein the rVg is produced in an insect expression system.

4. The method of claim 1, wherein the rVg has the amino acid sequence of SEQ ID NO: 1.

5. The method of claim 1, wherein the solid support is selected from a chromatographic support, a sepharose CL column, or an ion exchange column.

6. The method of claim 1, wherein the honey bee pathogens is inactivated by sonication or solubilization in non-ionic detergents.

7. The method of claim 1, wherein the honey bee pathogen is selected from one or more of *Paenibacillus larvae, Paenibacillus alvei, Paenibacillus dendritiformis Paenibacillus amylolyticus, Paenibacillus campinasensis, Paenibacillus chondroitinis, Paenibacillus chungangensis, Paenibacillus doosanensis, Paenibacillus glucanolyticus, Paenibacillus humicus, Paenibacillus lactis, Paenibacillus lautus, Paenibacillus lentimorbus, Paenibacillus maceran, Paenibacillus macerans*-like, *Paenibacillus macquariensis, Paenibacillus motobuensis, Paenibacillus pabuli, Paenibacillus phoenicis, Paenibacillus polymyxa, Paenibacillus popilliae, Paenibacillus puldeungensis, Paenibacillus residui, Paenibacillus stellife, Paenibacillus thiaminolyticus, Paenibacillus validus,* or *Paenibacillus xylanisolvens*.

8. The method of claim 7, wherein more than one honey bee pathogen is contacted with the column.

9. The method of claim 1, wherein the identity of the isolated inactivated honey bee pathogen is determined by a method comprising a combination of electrophoresis, high performance liquid chromatography, mass spectrometry, and/or protein sequencing.

10. The method of claim 1, wherein the inactivated honey bee pathogen is detectably labeled.

11. The method of claim 3, wherein the insect expression system is a baculovirus-insect cell system.

* * * * *